(12) United States Patent
Kaula et al.

(10) Patent No.: US 8,761,897 B2
(45) Date of Patent: Jun. 24, 2014

(54) METHOD AND SYSTEM OF GRAPHICAL REPRESENTATION OF LEAD CONNECTOR BLOCK AND IMPLANTABLE PULSE GENERATORS ON A CLINICIAN PROGRAMMER

(71) Applicant: Greatbatch Ltd., Clarence, NY (US)

(72) Inventors: Norbert Kaula, Arvada, CO (US); Yohannes Iyassu, Denver, CO (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/015,032

(22) Filed: Aug. 30, 2013

(65) Prior Publication Data

US 2014/0067020 A1 Mar. 6, 2014

Related U.S. Application Data

(63) Continuation-in-part of application No. 13/601,449, filed on Aug. 31, 2012.

(60) Provisional application No. 61/695,420, filed on Aug. 31, 2012.

(51) Int. Cl.
*A61N 1/00* (2006.01)

(52) U.S. Cl.
USPC .............................................. 607/60; 607/30

(58) Field of Classification Search
CPC .......................... A61B 5/0002; A61N 1/37247
USPC ...................................................... 607/30, 60
See application file for complete search history.

(56) References Cited

U.S. PATENT DOCUMENTS

| | | |
|---|---|---|
| 4,432,360 A | 2/1984 | Mumford et al. |
| 5,286,202 A | 2/1994 | De Gyarfas et al. |
| 5,304,206 A | 4/1994 | Baker, Jr. et al. |
| 5,312,446 A | 5/1994 | Holschbach et al. |

(Continued)

FOREIGN PATENT DOCUMENTS

| | | |
|---|---|---|
| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.

(Continued)

*Primary Examiner* — Nicole F Lavert
(74) *Attorney, Agent, or Firm* — Haynes and Boone, LLP

(57) ABSTRACT

The present disclosure involves a method of providing graphical representations of medical devices and connections between the medical devices. A graphical representation of a lead is displayed. The lead is configured to deliver electrical stimulation to a patient via one or more of a plurality of electrode contacts. A graphical representation of one of: an implantable pulse generator (IPG) or a lead connector block is displayed. The IPG and the lead connector block are each configured for coupling with the lead. In response to a user input, a graphical representation of a connection is generated. The connection is between the lead and one of: the IPG or the lead connector block. An actual connection between the lead and one of: the IPG or the lead connector block is monitored. A status of the actual connection between the lead and one of: the IPG or the connector block is then reported.

36 Claims, 19 Drawing Sheets

(56) References Cited

U.S. PATENT DOCUMENTS

| | | |
|---|---|---|
| 5,370,672 A | 12/1994 | Fowler et al. |
| 5,383,914 A | 1/1995 | O'Phelan |
| 5,421,830 A | 6/1995 | Epstein et al. |
| 5,628,776 A | 5/1997 | Paul et al. |
| 5,713,937 A | 2/1998 | Nappholz et al. |
| 5,722,999 A | 3/1998 | Snell |
| 5,724,996 A | 3/1998 | Piunti |
| 5,819,740 A | 10/1998 | Muhlenberg |
| 5,879,374 A | 3/1999 | Powers et al. |
| 5,905,500 A | 5/1999 | Kamen et al. |
| 5,938,690 A | 8/1999 | Law et al. |
| 6,016,447 A | 1/2000 | Juran et al. |
| 6,016,448 A | 1/2000 | Busacker et al. |
| 6,052,624 A | 4/2000 | Mann |
| 6,083,156 A | 7/2000 | Lisiecki |
| 6,148,233 A | 11/2000 | Owen et al. |
| 6,154,675 A | 11/2000 | Juran et al. |
| 6,216,036 B1 | 4/2001 | Jenkins et al. |
| 6,246,414 B1 | 6/2001 | Kawasaki |
| 6,249,705 B1 | 6/2001 | Snell |
| 6,278,890 B1 | 8/2001 | Chassaing et al. |
| 6,307,554 B1 | 10/2001 | Arai et al. |
| 6,308,102 B1 | 10/2001 | Sieracki et al. |
| 6,345,200 B1 | 2/2002 | Mouchawar et al. |
| 6,386,882 B1 | 5/2002 | Linberg |
| 6,442,432 B2 | 8/2002 | Lee |
| 6,525,727 B1 | 2/2003 | Junkins et al. |
| 6,564,104 B2 | 5/2003 | Nelson et al. |
| 6,587,104 B1 | 7/2003 | Hoppe |
| 6,611,267 B2 | 8/2003 | Migdal et al. |
| 6,622,048 B1 | 9/2003 | Mann et al. |
| 6,669,631 B2 | 12/2003 | Norris et al. |
| 6,786,405 B2 | 9/2004 | Wiedenhoefer |
| 6,852,080 B2 | 2/2005 | Bardy |
| 6,882,982 B2 | 4/2005 | McMenimen et al. |
| 6,895,280 B2 | 5/2005 | Meadows et al. |
| 6,920,360 B2 | 7/2005 | Lee et al. |
| 6,931,155 B1 | 8/2005 | Gioia |
| 6,961,448 B2 | 11/2005 | Nichols et al. |
| 6,961,617 B1 | 11/2005 | Snell |
| 7,003,349 B1 | 2/2006 | Andersson et al. |
| 7,034,823 B2 | 4/2006 | Dunnett |
| 7,058,453 B2 | 6/2006 | Nelson et al. |
| 7,060,030 B2 | 6/2006 | Von Arx et al. |
| 7,065,409 B2 | 6/2006 | Mazar |
| 7,066,910 B2 | 6/2006 | Bauhahn et al. |
| 7,076,303 B2 | 7/2006 | Linberg |
| 7,087,015 B1 | 8/2006 | Comrie et al. |
| 7,092,761 B1 | 8/2006 | Cappa et al. |
| 7,107,102 B2 | 9/2006 | Daignault et al. |
| 7,142,923 B2 | 11/2006 | North et al. |
| 7,181,286 B2 | 2/2007 | Sieracki et al. |
| 7,181,505 B2 | 2/2007 | Haller et al. |
| 7,184,837 B2 | 2/2007 | Goetz |
| 7,239,926 B2 | 7/2007 | Goetz |
| 7,266,412 B2 | 9/2007 | Stypulkowski |
| 7,299,085 B2 | 11/2007 | Bergelson et al. |
| 7,359,751 B1 | 4/2008 | Erickson et al. |
| 7,373,204 B2 | 5/2008 | Gelfand et al. |
| 7,440,806 B1 | 10/2008 | Whitehurst et al. |
| 7,452,336 B2 | 11/2008 | Thompson |
| 7,463,927 B1 | 12/2008 | Chaouat |
| 7,474,223 B2 | 1/2009 | Nycz et al. |
| 7,481,759 B2 | 1/2009 | Whitehurst et al. |
| 7,489,970 B2 | 2/2009 | Lee et al. |
| 7,496,403 B2 | 2/2009 | Cao et al. |
| 7,499,048 B2 | 3/2009 | Sieracki et al. |
| 7,505,815 B2 | 3/2009 | Lee et al. |
| 7,551,960 B2 | 6/2009 | Forsberg et al. |
| 7,602,384 B2 | 10/2009 | Rosenberg et al. |
| 7,617,002 B2 | 11/2009 | Goetz |
| 7,627,372 B2 | 12/2009 | Vaisnys et al. |
| 7,640,059 B2 | 12/2009 | Forsberg et al. |
| 7,657,317 B2 | 2/2010 | Thacker et al. |
| 7,685,005 B2 | 3/2010 | Riff et al. |
| 7,711,603 B2 | 5/2010 | Vanker et al. |
| 7,720,549 B2 | 5/2010 | Schroeppel et al. |
| 7,747,330 B2 | 6/2010 | Nolan et al. |
| 7,774,067 B2 | 8/2010 | Keacher et al. |
| 7,778,710 B2 | 8/2010 | Propato |
| 7,801,596 B2 | 9/2010 | Fischell et al. |
| 7,801,611 B2 | 9/2010 | Persen et al. |
| 7,805,199 B2 | 9/2010 | KenKnight et al. |
| 7,822,483 B2 | 10/2010 | Stone et al. |
| 7,853,323 B2 | 12/2010 | Goetz |
| 7,885,712 B2 | 2/2011 | Goetz et al. |
| 7,890,180 B2 | 2/2011 | Quiles et al. |
| 7,928,995 B2 | 4/2011 | Daignault |
| 7,934,508 B2 | 5/2011 | Behm |
| 7,940,933 B2 | 5/2011 | Corndorf |
| 7,953,492 B2 | 5/2011 | Corndorf |
| 7,953,612 B1 | 5/2011 | Palmese et al. |
| 7,957,808 B2 | 6/2011 | Dawant et al. |
| 7,978,062 B2 | 7/2011 | LaLonde et al. |
| 7,991,482 B2 | 8/2011 | Bradley |
| 8,014,863 B2 | 9/2011 | Zhang et al. |
| 8,021,298 B2 | 9/2011 | Barid et al. |
| 8,027,726 B2 | 9/2011 | Ternes |
| 8,046,241 B1 | 10/2011 | Dodson |
| 8,060,216 B2 | 11/2011 | Greenberg et al. |
| 8,068,915 B2 | 11/2011 | Lee et al. |
| 8,068,918 B2 | 11/2011 | Vallapureddy et al. |
| 8,078,440 B2 | 12/2011 | Otto et al. |
| 8,082,162 B2 | 12/2011 | Flood |
| 8,121,702 B2 | 2/2012 | King |
| 8,135,566 B2 | 3/2012 | Marshall et al. |
| 8,140,160 B2 | 3/2012 | Pless et al. |
| 8,140,167 B2 | 3/2012 | Donders et al. |
| 8,160,328 B2 | 4/2012 | Goetz et al. |
| 8,160,704 B2 | 4/2012 | Freeberg |
| 8,165,385 B2 | 4/2012 | Reeves et al. |
| 8,187,015 B2 | 5/2012 | Boyd et al. |
| 8,200,324 B2 | 6/2012 | Shen et al. |
| 8,200,340 B2 | 6/2012 | Skelton et al. |
| 8,219,206 B2 | 7/2012 | Skelton et al. |
| 8,233,991 B2 | 7/2012 | Woods et al. |
| 8,246,680 B2 | 8/2012 | Betz et al. |
| 8,249,713 B2 | 8/2012 | Fang et al. |
| 8,255,060 B2 | 8/2012 | Goetz et al. |
| 8,323,218 B2 | 12/2012 | Davis et al. |
| 8,326,433 B2 | 12/2012 | Blum et al. |
| 8,340,775 B1 | 12/2012 | Cullen et al. |
| 8,382,666 B1 | 2/2013 | Mao et al. |
| 8,386,032 B2 | 2/2013 | Bachinski et al. |
| 8,401,666 B2 | 3/2013 | Skelton et al. |
| 8,428,727 B2 | 4/2013 | Bolea et al. |
| 2001/0037220 A1 | 11/2001 | Merry et al. |
| 2003/0076301 A1 | 4/2003 | Tsuk et al. |
| 2003/0107572 A1 | 6/2003 | Smith et al. |
| 2003/0139652 A1 | 7/2003 | Kang et al. |
| 2003/0171911 A1 | 9/2003 | Fairweather |
| 2003/0177031 A1 | 9/2003 | Malek |
| 2004/0088374 A1 | 5/2004 | Webb et al. |
| 2004/0122477 A1 | 6/2004 | Whitehurst et al. |
| 2004/0210273 A1 | 10/2004 | Wang |
| 2005/0107831 A1 | 5/2005 | Hill et al. |
| 2005/0149356 A1 | 7/2005 | Cyr et al. |
| 2005/0168460 A1 | 8/2005 | Razdan et al. |
| 2005/0277872 A1 | 12/2005 | Colby et al. |
| 2006/0089888 A1 | 4/2006 | Roger |
| 2006/0100832 A1 | 5/2006 | Bowman |
| 2006/0241720 A1 | 10/2006 | Woods et al. |
| 2006/0242159 A1 | 10/2006 | Bishop et al. |
| 2006/0282168 A1 | 12/2006 | Sherman et al. |
| 2007/0078497 A1 | 4/2007 | Vandanacker |
| 2007/0093998 A1 | 4/2007 | El-Baroudi et al. |
| 2007/0179349 A1 | 8/2007 | Hoyme et al. |
| 2007/0203537 A1 | 8/2007 | Goetz et al. |
| 2007/0203538 A1 | 8/2007 | Stone et al. |
| 2007/0203543 A1 | 8/2007 | Stone et al. |
| 2007/0213790 A1 | 9/2007 | Nolan et al. |
| 2008/0004675 A1 | 1/2008 | King et al. |
| 2008/0033303 A1 | 2/2008 | Wariar et al. |
| 2008/0046036 A1 | 2/2008 | King et al. |

(56) References Cited

U.S. PATENT DOCUMENTS

| | | |
|---|---|---|
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgerson et al. |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennett et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Burdiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Conner et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

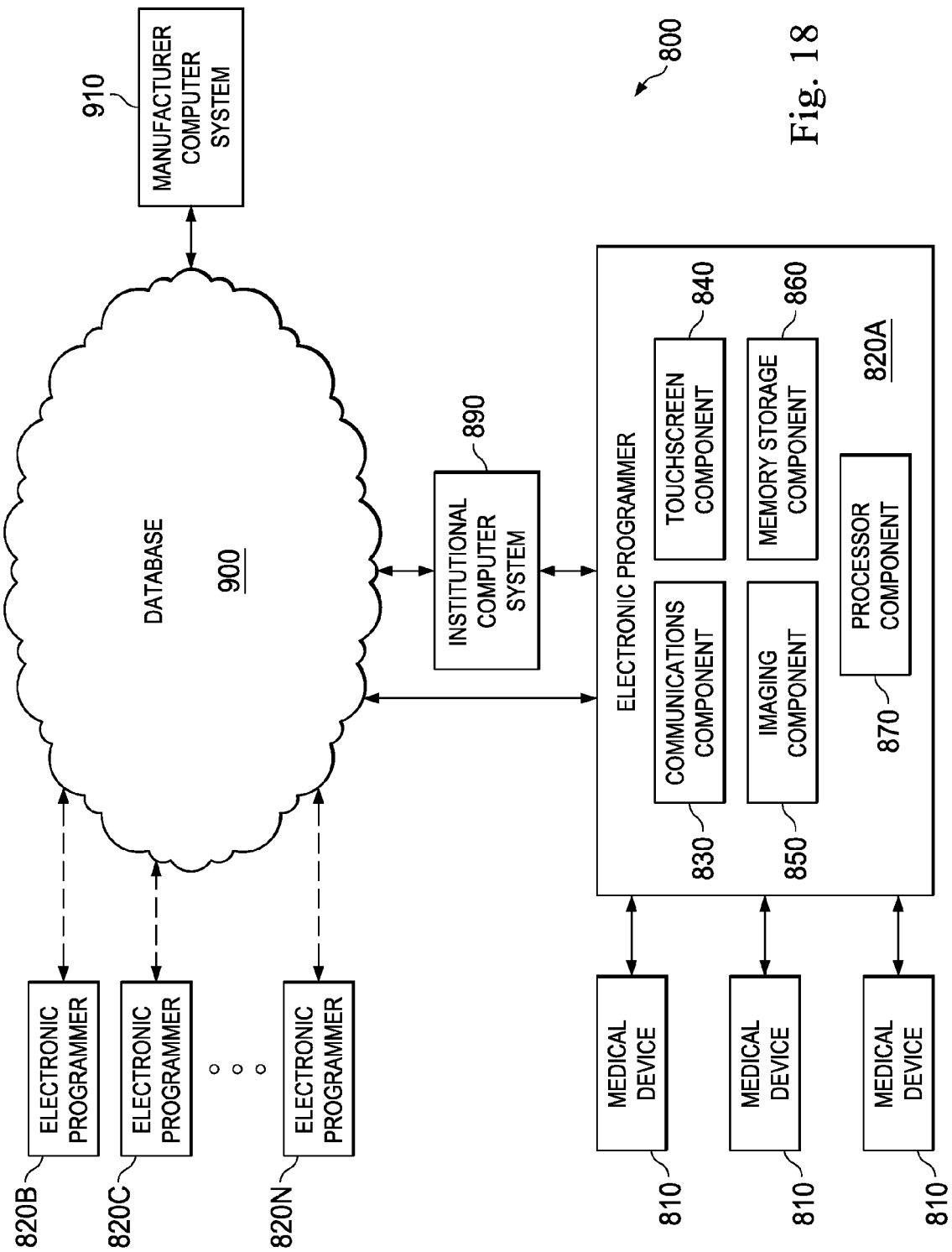

METHOD AND SYSTEM OF GRAPHICAL REPRESENTATION OF LEAD CONNECTOR BLOCK AND IMPLANTABLE PULSE GENERATORS ON A CLINICIAN PROGRAMMER

PRIORITY DATA

This application is a utility application of Provisional U.S. Patent Application No. 61/695,420, filed on Aug. 31, 2012, entitled "Method And System of Graphical Representation of Lead Connector Blocks and Implantable Pulse Generators on a Clinician Programmer", and a continuation-in-part of U.S. patent application Ser. No. 13/601,449, filed on Aug. 31, 2012, entitled "Virtual Reality Representation of Medical Devices", the disclosure of each of which is hereby incorporated by reference in its entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients.

An implanted medical device (for example a neurostimulator) can be controlled using an electronic programming device such as a clinician programmer or a patient programmer. These programmers can be used by medical personnel or the patient to define the particular electrical stimulation therapy to be delivered to a target area of the patient's body or alter one or more parameters of the electrical stimulation therapy. Advances in the medical device field have improved these electronic programmers. However, existing electronic programmers may still have shortcomings such as inadequate representation or visualization of medical devices. For example, existing electronic programmers may not allow a user to visualize the actual look of the stimulation implanted lead or the location or orientation of an implantable medical device within the appropriate anatomical surroundings of a patient.

Therefore, although electronic programming devices for controlling implanted medical devices have been generally adequate for their intended purposes, they have not been entirely satisfactory in every aspect.

SUMMARY

The present disclosure involves an electronic device configured to provide graphical representations of medical devices and connections between the medical devices. The electronic device includes a touch-sensitive display configured to receive input from a user and display an output to the user. The electronic device includes a memory storage component configured to store programming code. The electronic device includes a computer processor configured to execute the programming code to perform the following tasks: displaying, via the touch-sensitive display, a graphical representation of a lead, the lead being configured to deliver electrical stimulation to a patient via one or more of a plurality of electrode contacts located on the lead; displaying, via the touch-sensitive display, a graphical representation of one of: an implantable pulse generator (IPG) or a lead connector block, wherein the IPG and the lead connector block are each configured for coupling with the lead; generating, in response to a user input, a graphical representation of a connection between the lead and one of: the IPG or the lead connector block; monitoring an actual connection between the lead and one of: the IPG or the lead connector block; and reporting a status of the actual connection between the lead and one of: the IPG or the connector block.

The present disclosure also involves a medical system. The medical system includes a pulse generator configured to generate pulses as part of an electrical stimulation therapy for a patient. The medical system includes a lead having a plurality of electrode contacts, the lead being configured for coupling with the pulse generator and for delivering the pulses to the patient via one or more of the electrode contacts. The medical system includes a clinician programmer configured to provide a graphical representation of the pulse generator, the lead, and connections therebetween. The clinician programmer includes one or more processors and a non-transitory, tangible machine-readable storage medium storing a computer application. The computer application contains machine-readable instructions that when executed electronically by the one or more processors, perform the following actions: displaying, via a touch-sensitive graphical user interface of the clinician programmer, a graphical representation of the pulse generator, a graphical representation of the lead; generating, in response to a user input, a graphical representation of a connection between the lead and the pulse generator; monitoring an actual connection between the lead and the pulse generator; and reporting a status of the actual connection between the lead and the pulse generator.

The present disclosure further involves a method of providing graphical representations of medical devices and connections between the medical devices. The method includes: displaying, via a touch-sensitive graphical user interface of a portable electronic device, a graphical representation of a lead, the lead being configured to deliver electrical stimulation to a patient via one or more of a plurality of electrode contacts located on the lead; displaying, via the graphical user interface, a graphical representation of one of: an implantable pulse generator (IPG) or a lead connector block, wherein the IPG and the lead connector block are each configured for coupling with the lead; generating, in response to a user input, a graphical representation of a connection between the lead and one of: the IPG or the lead connector block; monitoring an actual connection between the lead and one of: the IPG or the lead connector block; and reporting a status of the actual connection between the lead and one of: the IPG or the connector block.

The present disclosure also involves an electronic apparatus for providing graphical representations of medical devices and connections between the medical devices. The electronic apparatus includes user interface means for communicating with a user. The electronic apparatus includes memory storage means for storing executable instructions. The electronic apparatus includes computer processor means for executing the instructions to perform: displaying, via the user interface means, a graphical representation of a lead over a graphical representation of a human spinal cord, the lead being configured to deliver electrical stimulation to a patient via one or more of a plurality of electrode contacts located on the lead; displaying, via the user interface means, a graphical representation of one of: an implantable pulse generator (IPG) or a lead connector block, wherein the IPG and the lead connector block are each configured for coupling with the lead; generating, in response to a user input, a graphical representation of a connection between the lead and one of: the IPG or the lead connector block; establishing a communications link with one of: the IPG or the lead connector block; monitoring an actual connection between the lead and one of: the IPG or the lead connector block, wherein the monitoring comprises performing an impedance check for each of the electrode contacts on the lead; and reporting a status of the actual connection between the lead and one of: the IPG or the connector block, wherein the reporting comprises visually indicating electrode contacts that are problematic.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 18 is a simplified block diagram of a medical system/infrastructure according to various aspects of the present disclosure.

DETAILED DESCRIPTION

Figure 1:
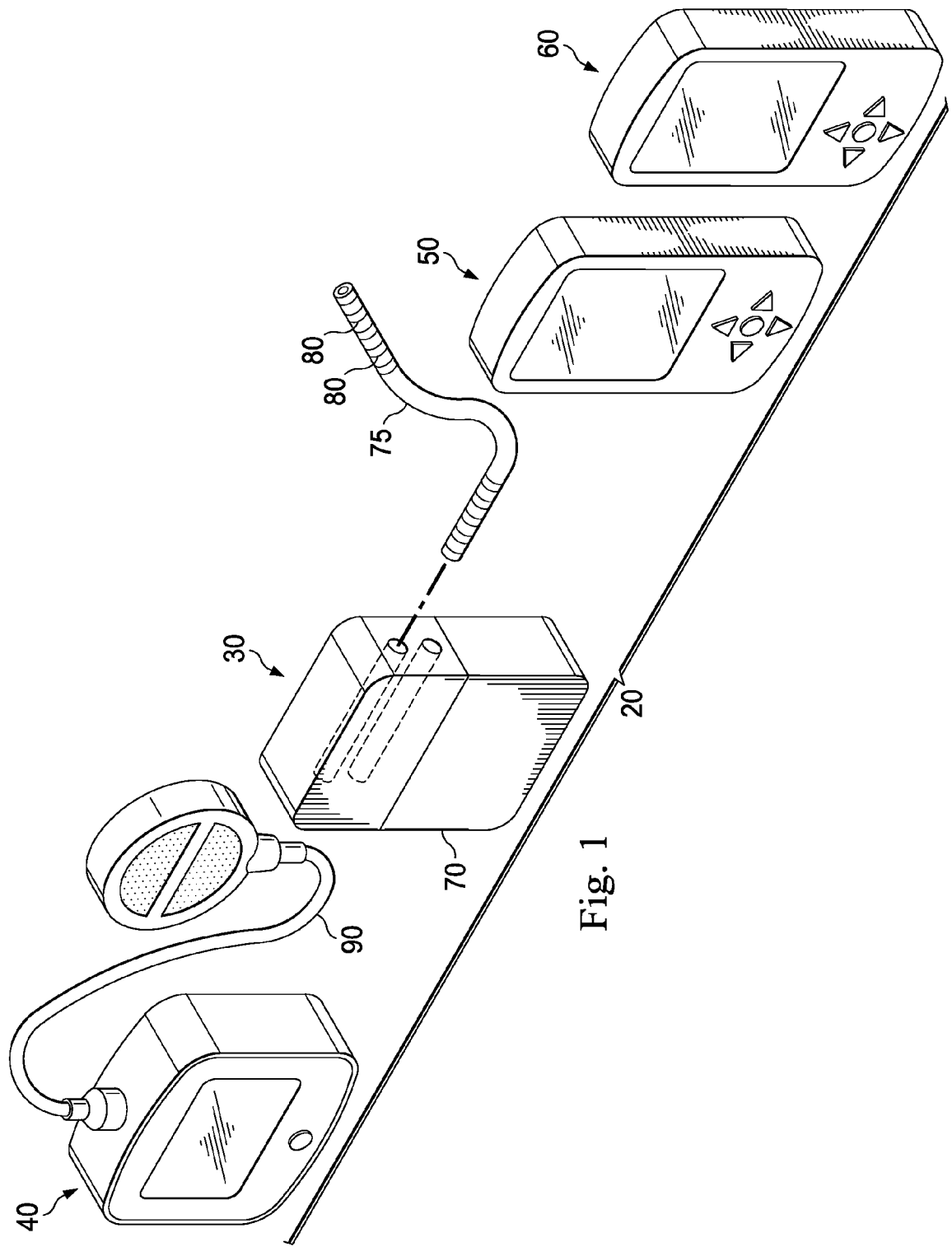
FIG. 1 is a simplified block diagram of a medical system according to various aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

The use of active implanted medical devices has become increasingly prevalent over time. Some of these implanted medical devices include neurostimulator devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

In recent years, these electronic programmers have achieved significant improvements, for example, improvements in size, power consumption, lifetime, and ease of use. Despite these advances, however, existing electronic programmers have not been sufficiently used to help healthcare professionals visualize their work. For example, in the field of electrical neural stimulation or the subfield of spinal cord stimulation, it may be useful to provide a visualization of implanted leads, which contain sets of electrodes to deliver the electrical pulses to the spinal cord and pulse generators to generate the pulses. In most cases, the lead is implanted next to the patient's spinal cord and connected to a lead connector block that is connected to an external pulse generator. After a trial period, an implantable pulse generator is implanted in the patient and connected directly to the lead(s). Unfortunately, healthcare professionals currently have no way of visualizing any part of this process on computers, particularly on clinician programmers.

As such, the shortcomings of the lack of visualization on existing electronic programmers are as follows:

The connections between the lead(s) and the connector blocks or pulse generators are not displayed.

Information about connection quality (i.e., whether the electrical pulses are being transmitted fully) is not displayed visually.

There is no way to tell when a lead is being connected incorrectly.

Manual connection errors are not detectable.

Consequently, users (e.g., healthcare professionals) must mentally associate the implanted leads and the connection ports the leads are connected to.

To address the issues discussed above, the present disclosure offers methods and systems for illustrating connections between virtual representations of leads and lead connector blocks or implantable pulse generators (IPGs), as well as showing the quality of the electrical connection between them, which may be beneficial during implantation of leads. The various aspects of the present disclosure are discussed below in more detail.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

FIGS. 2-12 illustrate an example user interface 100 of an embodiment of the clinician programmer 60. The user interface 100 is intended for a target user, which may be a healthcare professional, for example a surgeon or a doctor. The user and the healthcare professional are interchangeably referred in the following paragraphs, but it is understood that they need not necessarily be the same entity.

Figure 2:
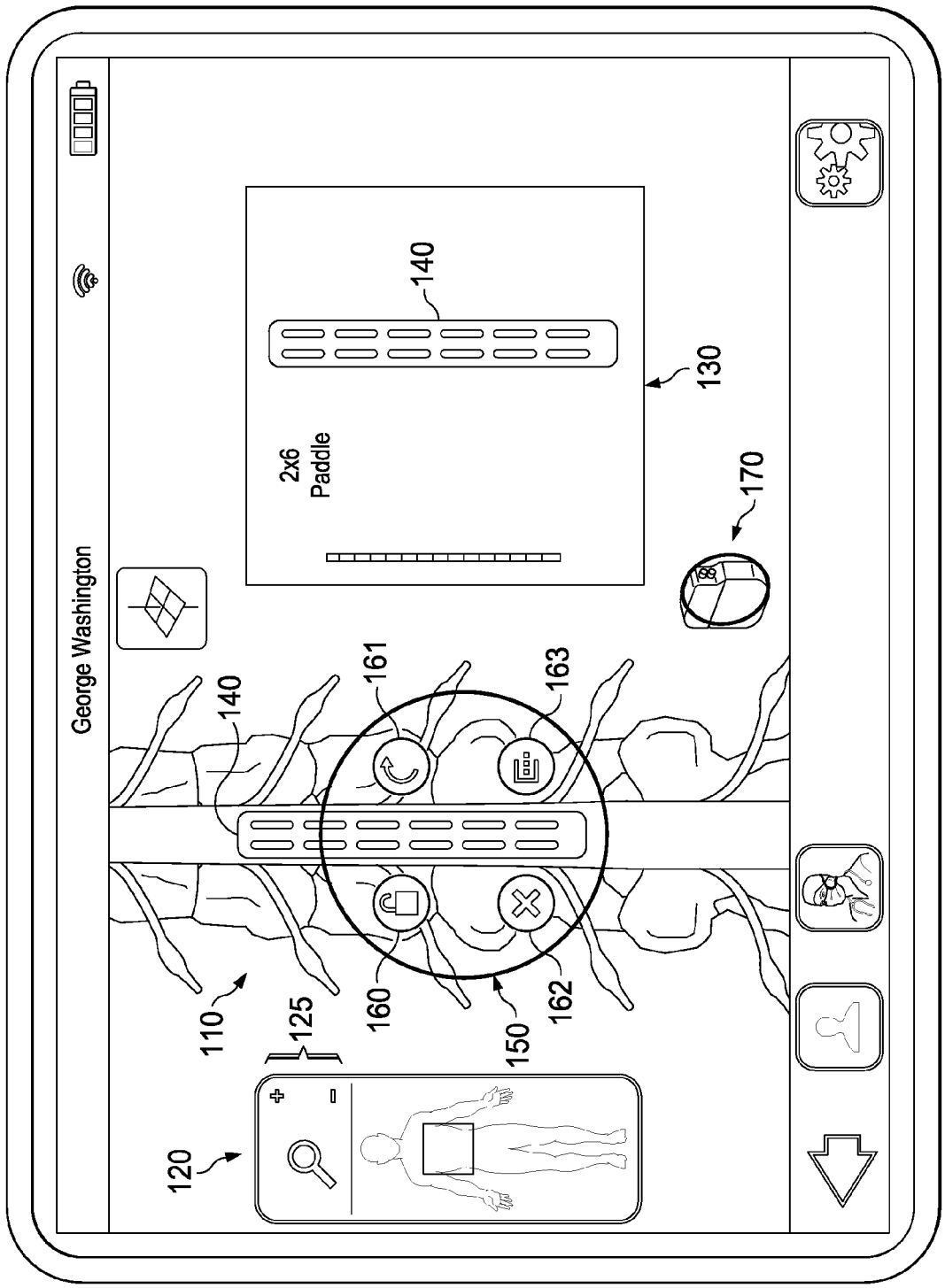
FIGS. 2-8, 9A-9D, and 10-12 are various example user interfaces for visualizing medical devices and the connections therebetween according to various aspects of the present disclosure.
Figure 3:
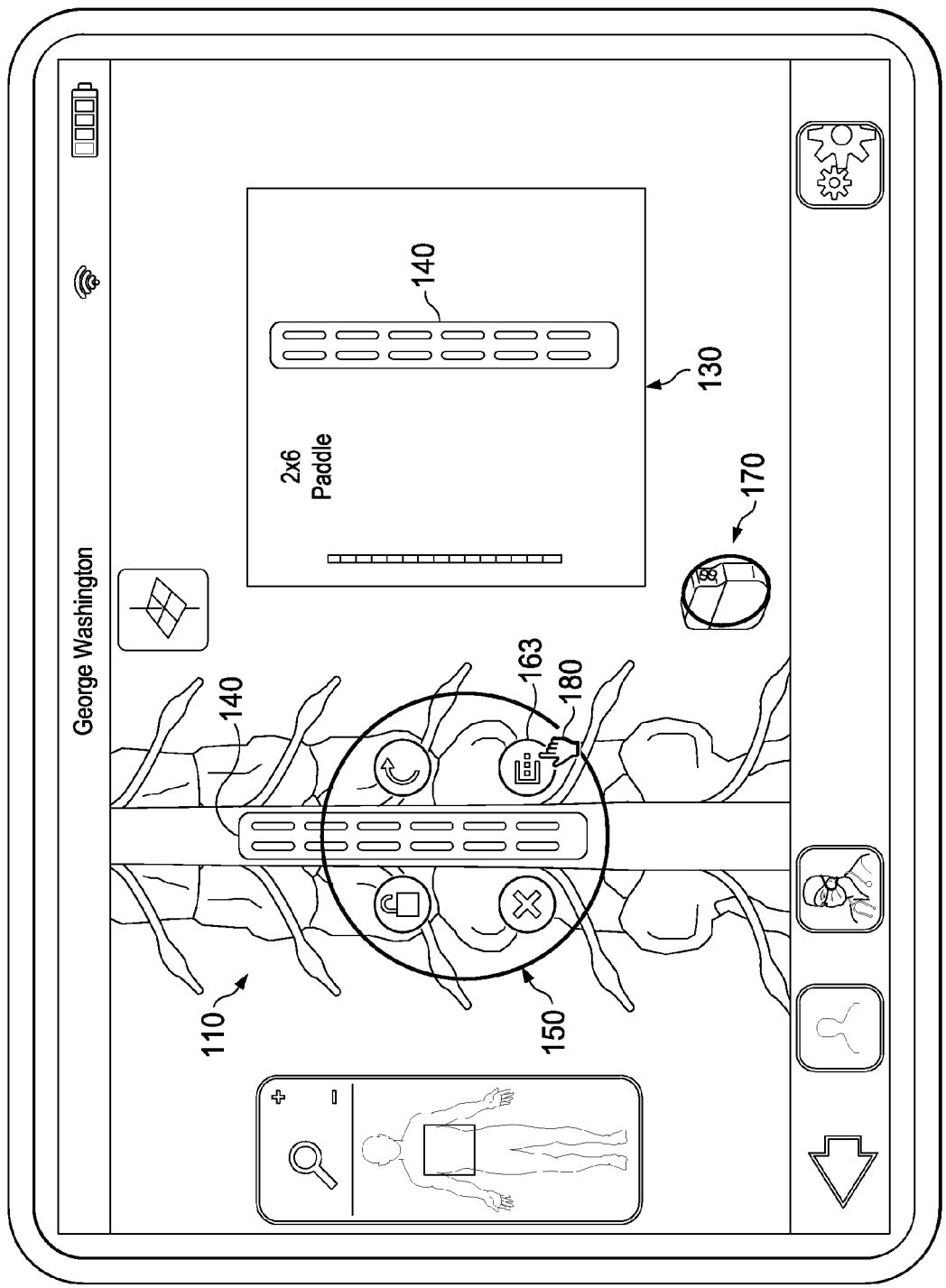

Referring to FIG. 2, the user interface 100 displays a virtual reality representation of an anatomical environment 110 (also referred to as anatomical surroundings) of a patient. The virtual reality representation of the anatomical environment 110 may involve 3-D or 2-D models. In the embodiment shown in FIG. 2, the anatomical environment 110 includes a portion of a spine. In other embodiments, the anatomical environment 110 may include other parts of the human body, for example the brain, the heart, or the abdomen, etc.

In some embodiments, the patient's physiological data (for example the patient's height or weight) is obtained by detecting user input through the user interface 100. In other embodiments, the patient's physiological data may be obtained or through another suitable mechanism such as from an electronic database, which can be remote or local to the programmer. According to the various aspects of the present disclosure, the virtual reality representation of the anatomical environment 110 may be customized in response to the patient's physiological data. For example, the spine (or another implementation of the anatomical environment) may be scaled based on the height of the patient.

The user interface 100A also includes a graphical display 120 that shows an entire human body (simulating the patient's body). A portion of the human body corresponding to the anatomical environment 110 is highlighted by a box superimposed on the human body. The user can quickly access a particular location of the human body by moving the box to that location. As the box is being moved, the anatomical environment 110 is updated to reflect the change. The user interface 110 also offers a zoom feature 125 that can be used to show a closer view (by zooming in) or a farther view (by zooming out) of the human body in the graphical display 120.

In other words, when the zoom feature 125 is activated to zoom in the human body, a more detailed view (e.g., showing fewer vertebrae) of the anatomical environment 110 is shown. Conversely, when the zoom feature 125 is activated to zoom out of the human body, a less detailed view (e.g., showing more vertebrae) of the anatomical environment 110 is shown.

The user interface 100 further includes a digital carousel 130 that shows the virtual reality representations of a plurality of medical devices. The virtual reality representation of each medical device may include an accurate movable and individually rotatable 3-D model of the medical device. The medical devices may be of different types, for example different types of leads, paddles, and pulse generators (including both implantable pulse generators (IPG) and external pulse generators (EPG).) These different types of medical devices are arranged in the carousel 130, which is spinnable. As the user spins the carousel 130, for example by moving his finger to the left or right on the touch screen, the models of different medical devices may be brought to the front of the carousel 130. The medical device at the front of the carousel 130 may be considered a temporary active selection from the user.

In the embodiment shown in FIG. 2, a paddle of a lead 140 (e.g., a 2×6 paddle lead having 12 electrodes) is displayed at the front of the carousel 130 and may be considered an active selection. Additional aspects of the digital carousel 130 are discussed in more detail in U.S. patent application Ser. No. 13/601,449, filed on Aug. 31, 2012, entitled "Virtual Reality Representation of Medical Devices", the disclosure of which is hereby incorporated by reference in its entirety. For reasons of simplicity, the paddle of the lead 140 may hereinafter be referred to as the lead 140, but it is understood that the actual lead includes not just the paddle shown in FIG. 2 but also an elongated lead wire (not illustrated).

The lead 140 may be placed (for example by dragging) in a desired location in the virtual reality representation of the anatomical environment 110 (i.e., the spinal cord). The user may trigger the display of an options menu 150 by touching and holding the lead 140 once the lead 140 has been properly positioned on the spinal cord. In the illustrated embodiment, the options menu 150 includes a set of icons 160-163 each disposed within a circle, but it is understood that the options menu 150 may assume other forms in alternative embodiments. In the illustrated embodiment, the icon 160 allows the lead 140 to be locked, the icon 161 allows the lead 140 to be rotated, the icon 162 allows the lead 140 to be deleted, and the icon 153 allows a simulated connection to be generated to connect the lead 140 to another medical device.

In the illustrated embodiment, the simulated connection is to be made with a pulse generator, for example an IPG 170 in this case. However, the simulated connection may also be made with a lead connector block used in conjunction with an EPG in other embodiments. The IPG 170 may be selected from the digital carousel 130. To initiate the simulated connection process, referring to FIG. 3, where the user engages the icon 163 via a simulated cursor 180. In other words, the user may click or press on the icon 163, which is illustrated by the simulated cursor 180 being moved over the icon 163.

Figure 4:
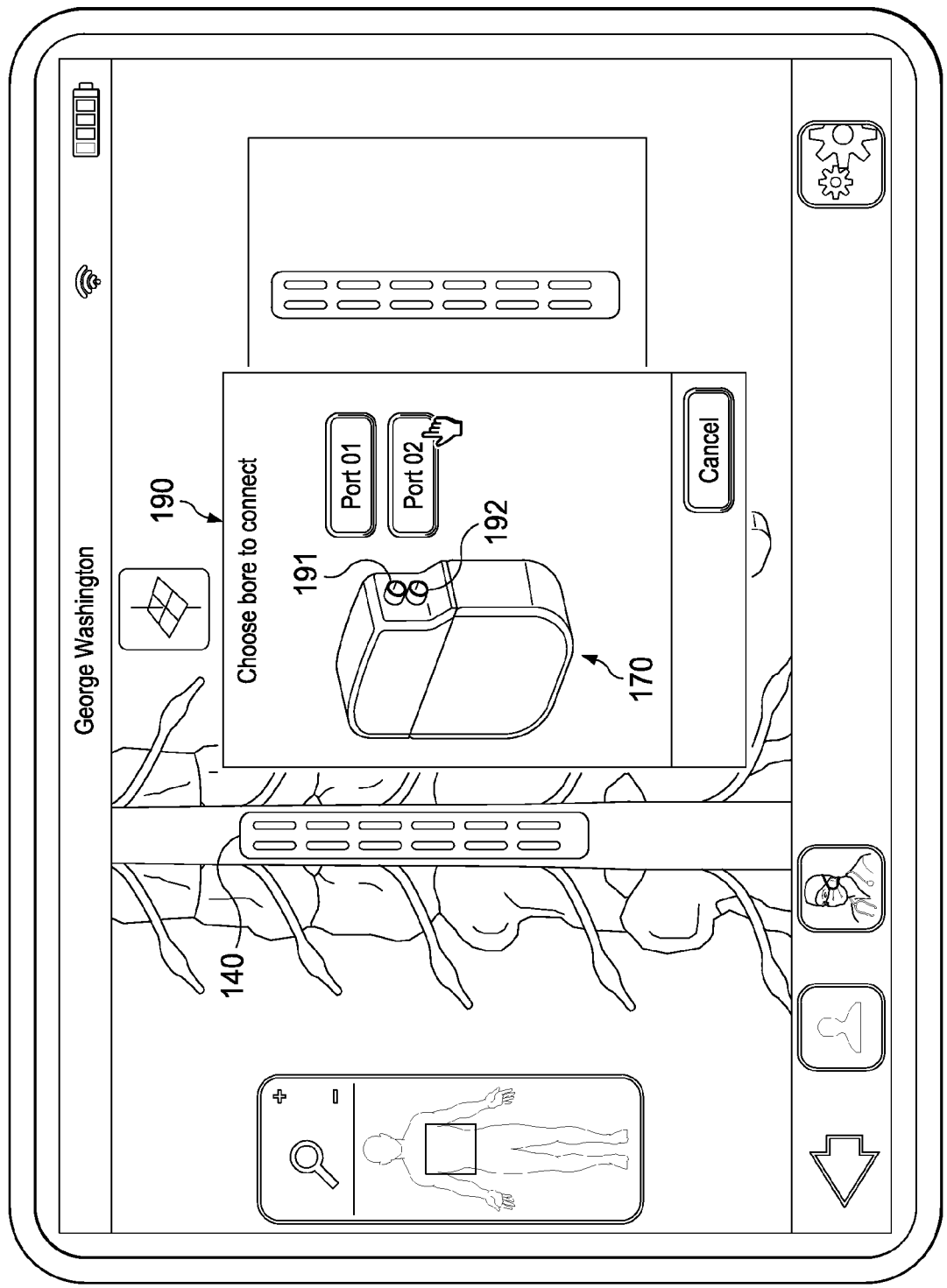
Figure 5:
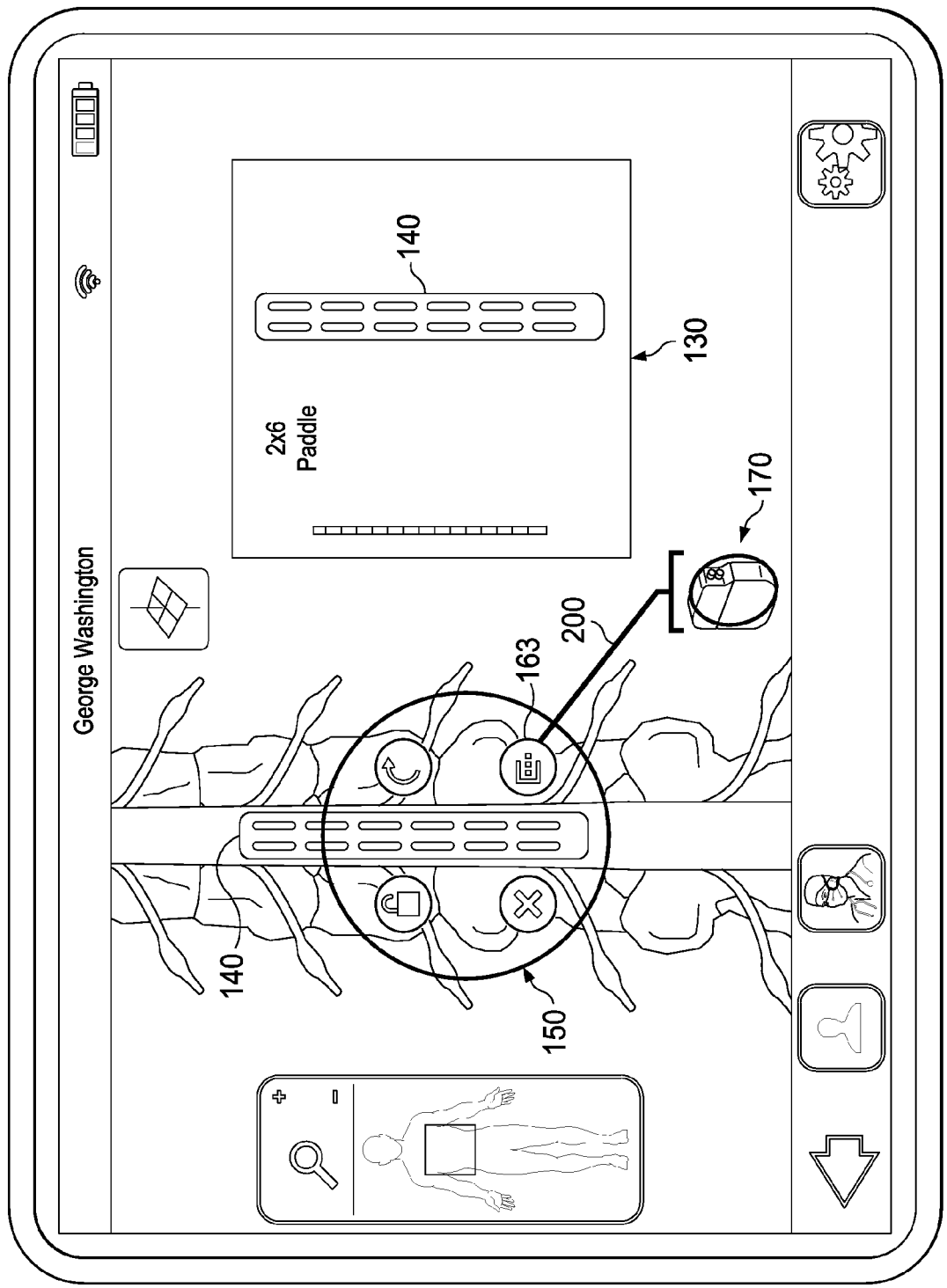

Referring now to FIG. 4, the engagement with the icon 163 triggers the display of a window 190. The window 190 contains a detailed and realistic illustration of the IPG 170. The IPG 170 in the illustrated embodiment includes two ports (also referred to as bores) 191 (Port 01) and 192 (Port 02). The user may then select which of the ports 191 and 192 the connection to the IPG 170 should be made. After the user selects the specific port on the IPG 170, a simulated connection 200 is automatically generated between the IPG 170 and the lead 140, as shown in FIG. 5.

Figure 6:
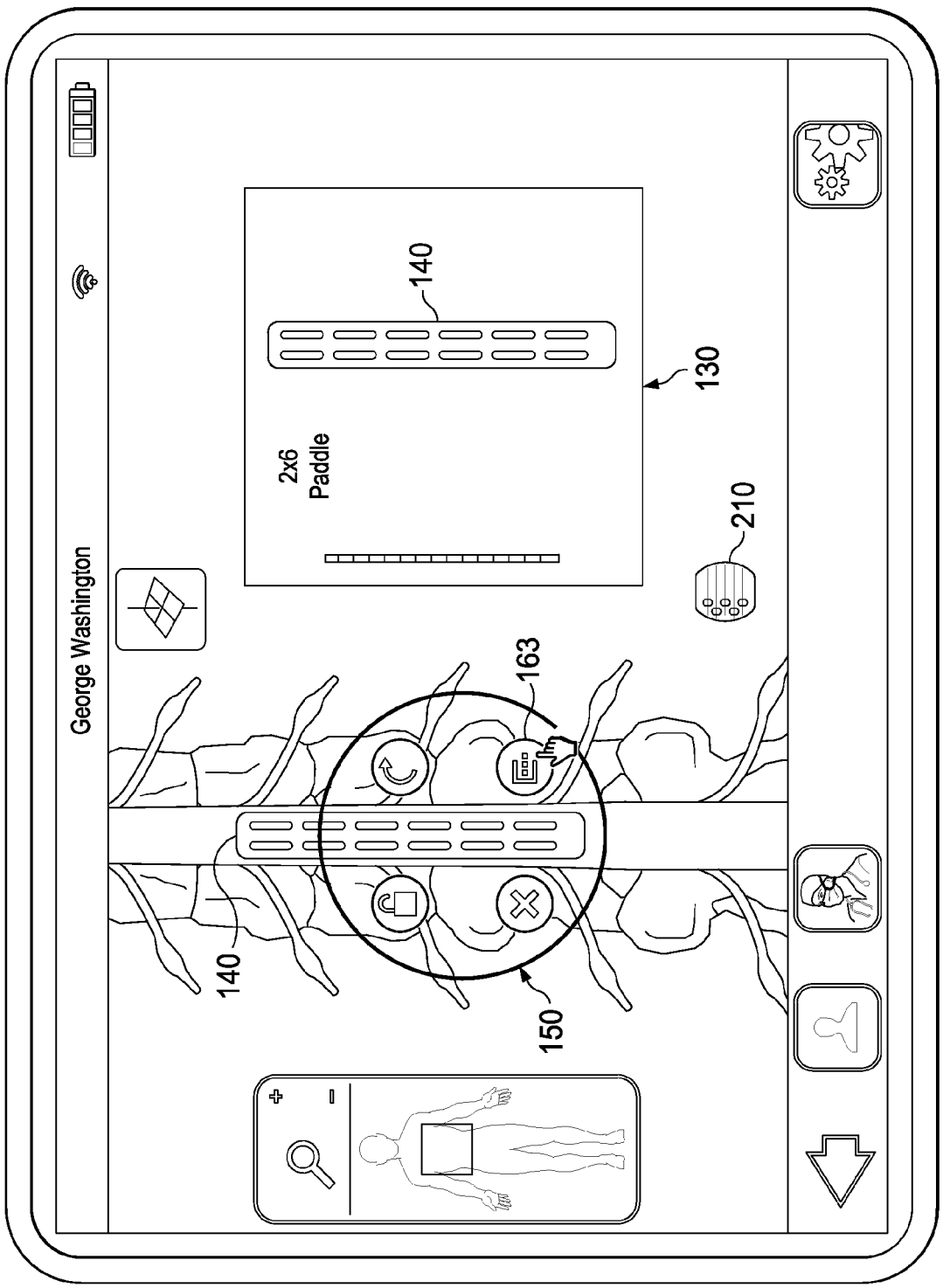
Figure 7:
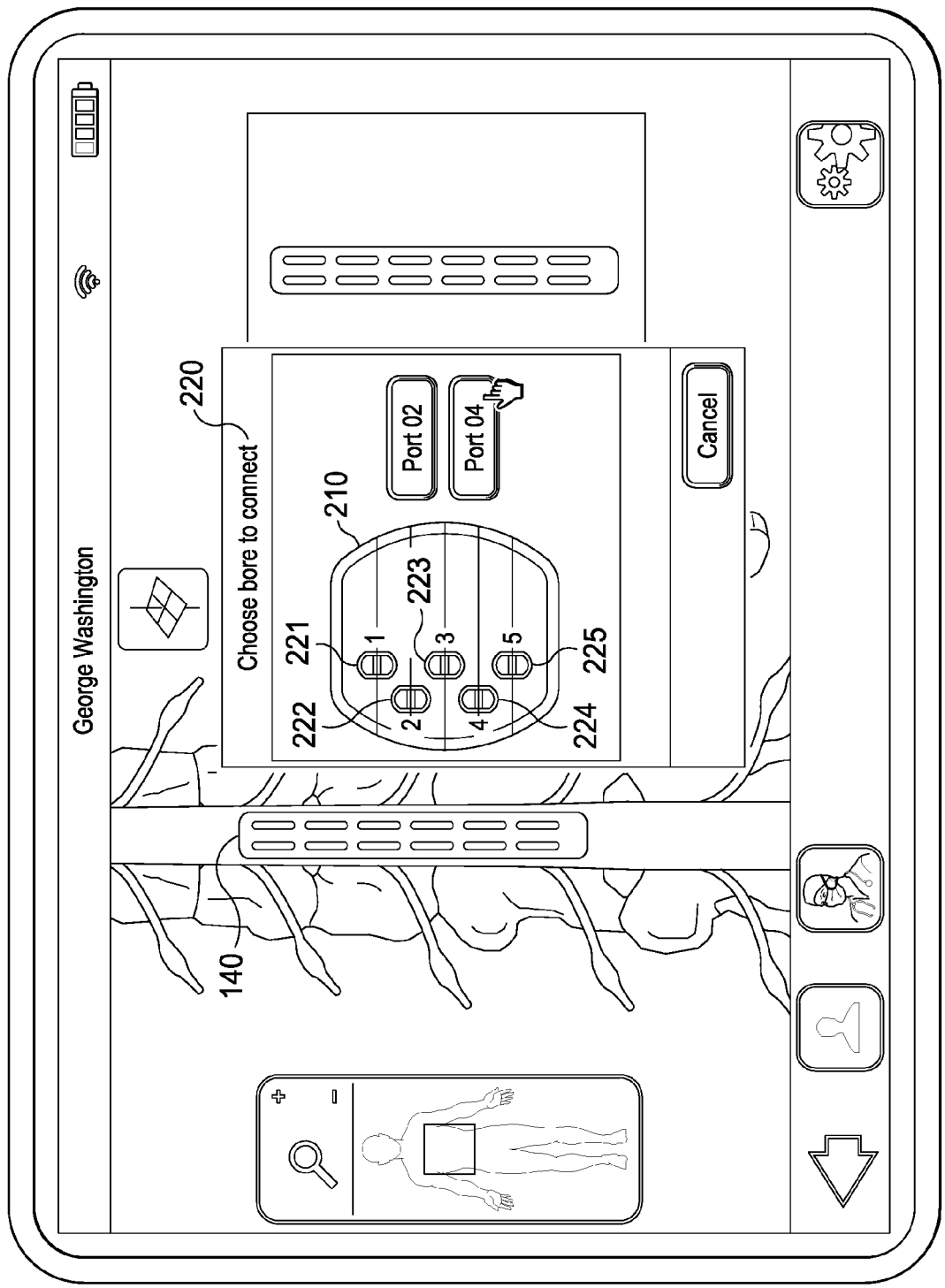
Figure 8:
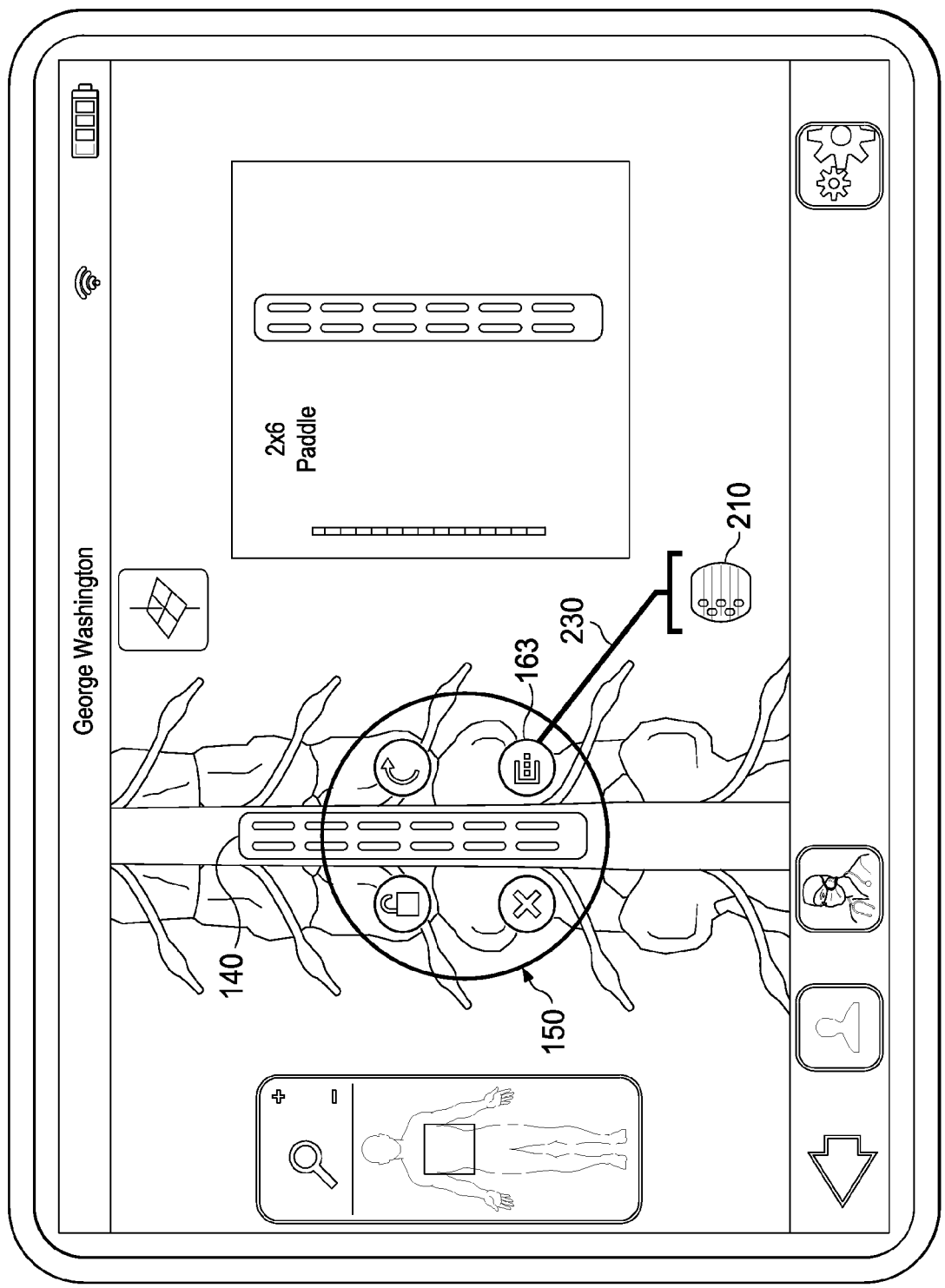

FIGS. 2-5 illustrate a process for connecting the lead 140 with the IPG 170. A similar process may also be used to establish a simulated connection between the lead 140 and a lead connector block 210, as shown in FIGS. 6-8. Referring to FIG. 6, the user may select the lead connector block 210 from the carousel 130. Thereafter, the user may trigger the display of the options menu 150 by touching and holding the lead 140, which has already been properly positioned on the spinal cord.

The user engages with the icon 163 to trigger the display of a window 220, which is shown in FIG. 7. The window 220 contains a detailed and realistic illustration of the lead connector block 210. The lead connector block 210 in the illustrated embodiment includes five ports (also referred to as bores) 221-225 (Ports 01-05). However, only ports 222 and 224 (Ports 02 and 04) are available here, as they are the two ports compatible with the 12-contact lead 140. In other words, the ports 221-225 of the lead connector block 210 may include a plurality of ports or bores that may each be configured to accommodate (or be connected to) a specific type of lead. The present disclosure automatically detects the type of lead (i.e., the lead 140) that is to be connected, and only the ports/bores compatible with that lead will be shown as being available on the lead connector block 210.

Referring now to FIG. 8, after the user selects the port (port 222 or port 224) of the lead connector block 210 for making the connection to the lead 140, a simulated connection 230 is automatically generated between that selected port and the lead 140.

It is understood that the simulated connections between the lead 140 and the IPG 170 or the lead connector block 210 discussed above are meant to represent the actual connections between these devices. In some embodiments, the user interface 100 may also be configured to display, with detail and clarity, the specific ports or bores to which the simulated connection 200/230 is made. For example, FIGS. 9A-9D illustrate an example process of simulating the connection between the lead 140 and the IPG 170 with detail and clarity.

Figure 9A:
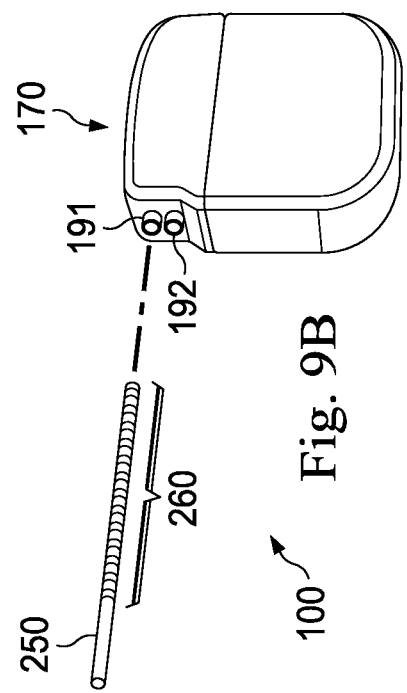

Referring to FIG. 9A, accurate virtual representations of a lead wire 250 and the IPG 170 are shown. The lead wire 250 is attached to the paddle of the lead 140 illustrated in FIGS. 2-8. The lead wire 250 and the paddle of the lead 140 collectively make up the "lead." For reasons of simplicity, the paddle of the lead 140 is not illustrated in FIGS. 9A-9D, but it is understood that it may optionally be illustrated in other embodiments. The lead wire 250 includes a plurality of conductive connectors 260 (twelve in this case) that are each electrically coupled to a respective one of the twelve electrode contacts on the paddle. In some embodiments, the conductive connectors 260 are metal rings or metal bands.

Figure 9B:
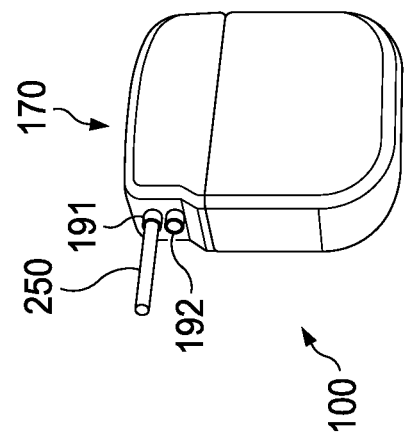
Figure 9C:
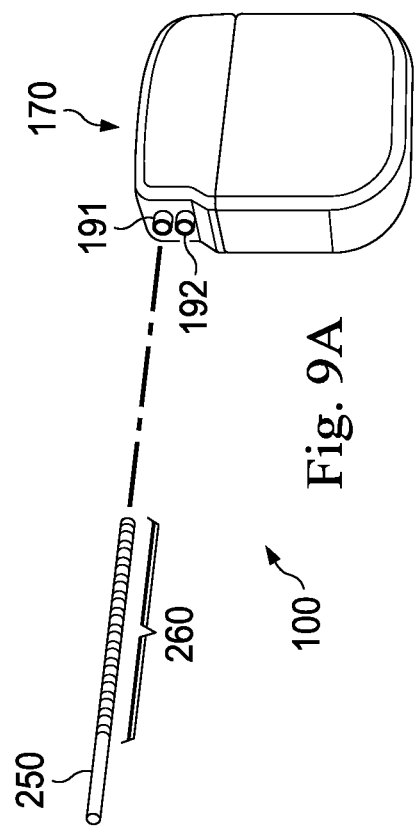
Figure 9D:
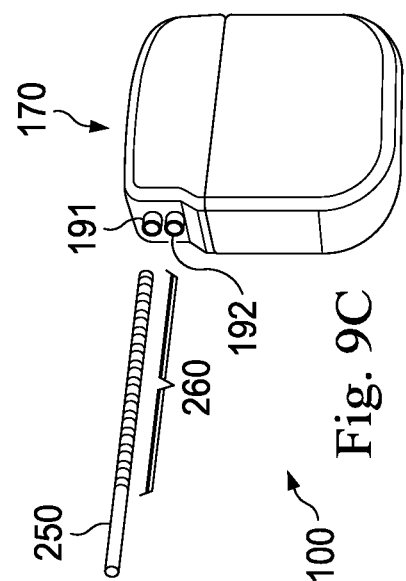

The virtual representation of the IPG 170 also includes the ports 191-192. In FIG. 9A, the lead wire 250 is still at a relatively far distance from the ports 191-192 of the IPG 170. In FIGS. 9B and 9C, the lead wire 250 moves closer to the IPG 170, specifically, to the port 191 of the IPG 170. This is in response to the user having selected the port 191 to be connected to the lead wire 250. Finally, as shown in FIG. 9D, the lead wire 250 is successfully connected to the port 191 of the IPG 170. In other words, the virtual representation of the lead wire 250 is inserted into the port 191 of the IPG 170, such that every one of the twelve conductive connectors 260 on the lead wire 250 is supposed to make electrical contact with a corresponding electrode inside the port 191 of the IPG 170.

In some embodiments, the process illustrated in FIGS. 9A-9D may be shown as a short animation sequence. Such animation sequence may be integrated into, or shown separately from, the simulated connections process shown in FIGS. 2-8. For example, in some embodiments, the animation sequence may be displayed after the simulated connection 200 is established. In other embodiments, the simulated connection 200 itself may be configured to resemble the lead wire 250. The lead wire 250 may be automatically connected to the target port of the IPG 170 in the same manner that the simulated connections 200 is made, or the user may be allowed to move or otherwise manipulate the lead wire 250 to make the connection with the target port of the IPG 170.

In some embodiments, after the lead wire 250 has been successfully inserted into the target port on the IPG 170, the user interface 100 will provide a recognizable feedback to the user. As examples, the feedback may be audible (e.g., a clicking sound or another suitable sound), tactile (e.g., a haptic response), or visual (e.g., an animated notification or just a highlighting of the target port on the IPG 170). In this manner, the user is informed that the simulated connection between the lead wire 250 and the IPG 170 has been successfully established.

In some embodiments, the user interface 100 will prevent the lead wire 250 from being inserted into the target port of the IPG until the actual connection is made between the lead wire and the IPG. In that case, the lead wire 250 may be stopped before being inserted into the port 191, for example it may be suspended in a state depicted in FIG. 9C. When the actual lead wire (represented by the lead wire 250) is inserted into the port (represented by the port 191), then the user interface 100 will be updated to reflect the actual connection being made. For example, the lead wire 250 may now be automatically inserted into the port 191 (such as shown in FIG. 9D), and the insertion may be accompanied by an audible sound or notification (e.g., a click) in some embodiments.

It is understood that although the IPG 170 used herein as an example to illustrate with detail and clarity how to make a connection with the lead wire 250, a lead connector block may be used in another embodiment instead of the IPG 170. In other words, the animation sequence discussed above with reference to FIGS. 9A-9D may apply with the lead connector block as well.

Figure 10:
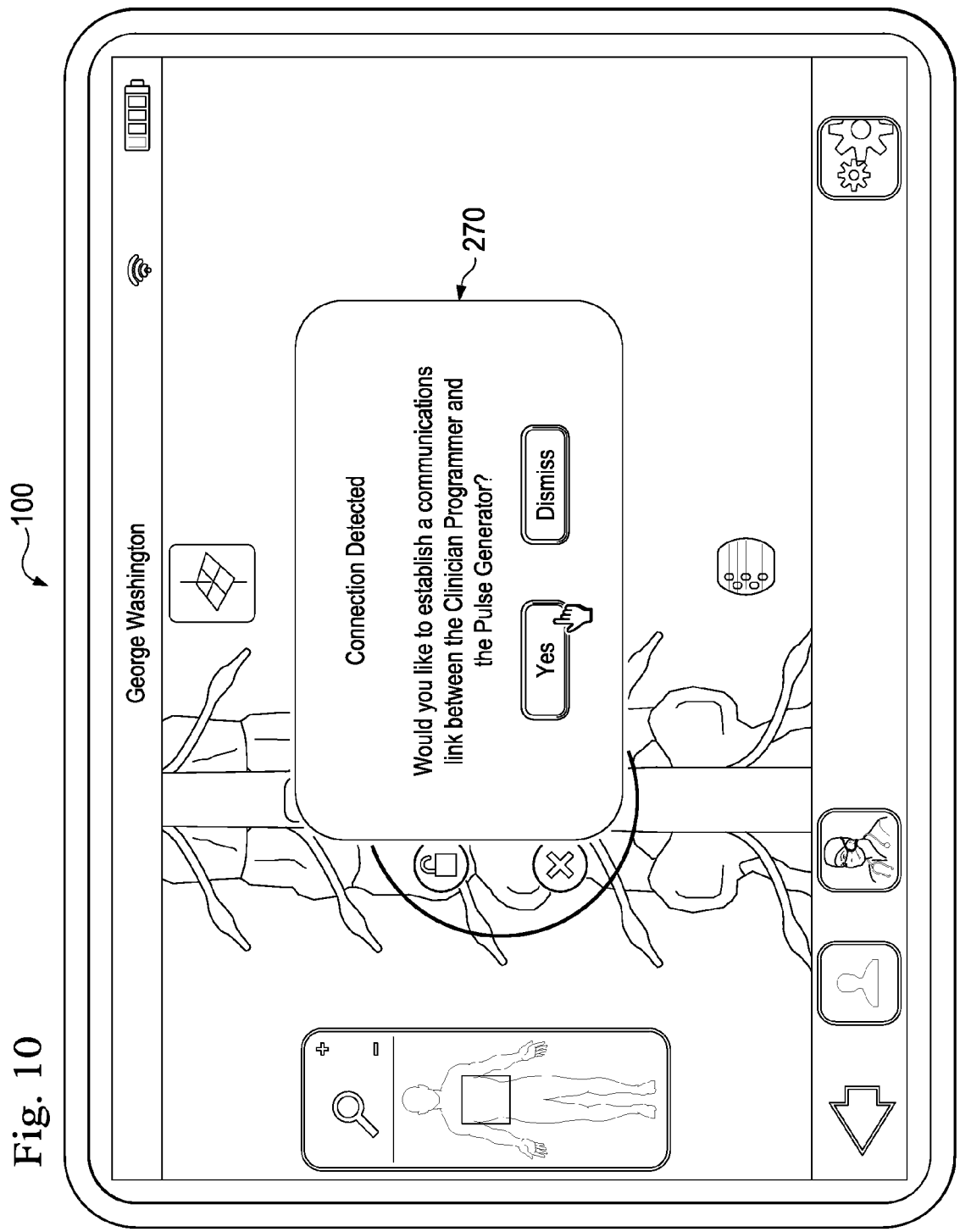

As discussed above, the simulated connections 200/230 represent the actual connections between a lead and an IPG or a lead connector block. To ensure that the simulated connection truthfully and accurately reflects the status of the actual connections, the clinician programmer may establish a communications link with the IPG or the lead connector block. For example, as shown in FIG. 10, the user interface 100 automatically displays a window 270. The window 270 may display a message asking if the user wishes to establish a communications link between the clinician programmer and the pulse generator (e.g., IPG). In some embodiments, the window 270 is automatically triggered after the simulated connection 200 between the lead 140 and the IPG 170 has been made. In other embodiments, the window 270 may be manually invoked before the simulated connection 200 between the lead 140 and the IPG has been made. For example, the user may choose to establish a communications link between the clinician programmer and the IPG or another external medical device before making the simulated connections via the user interface 100.

Figure 11:
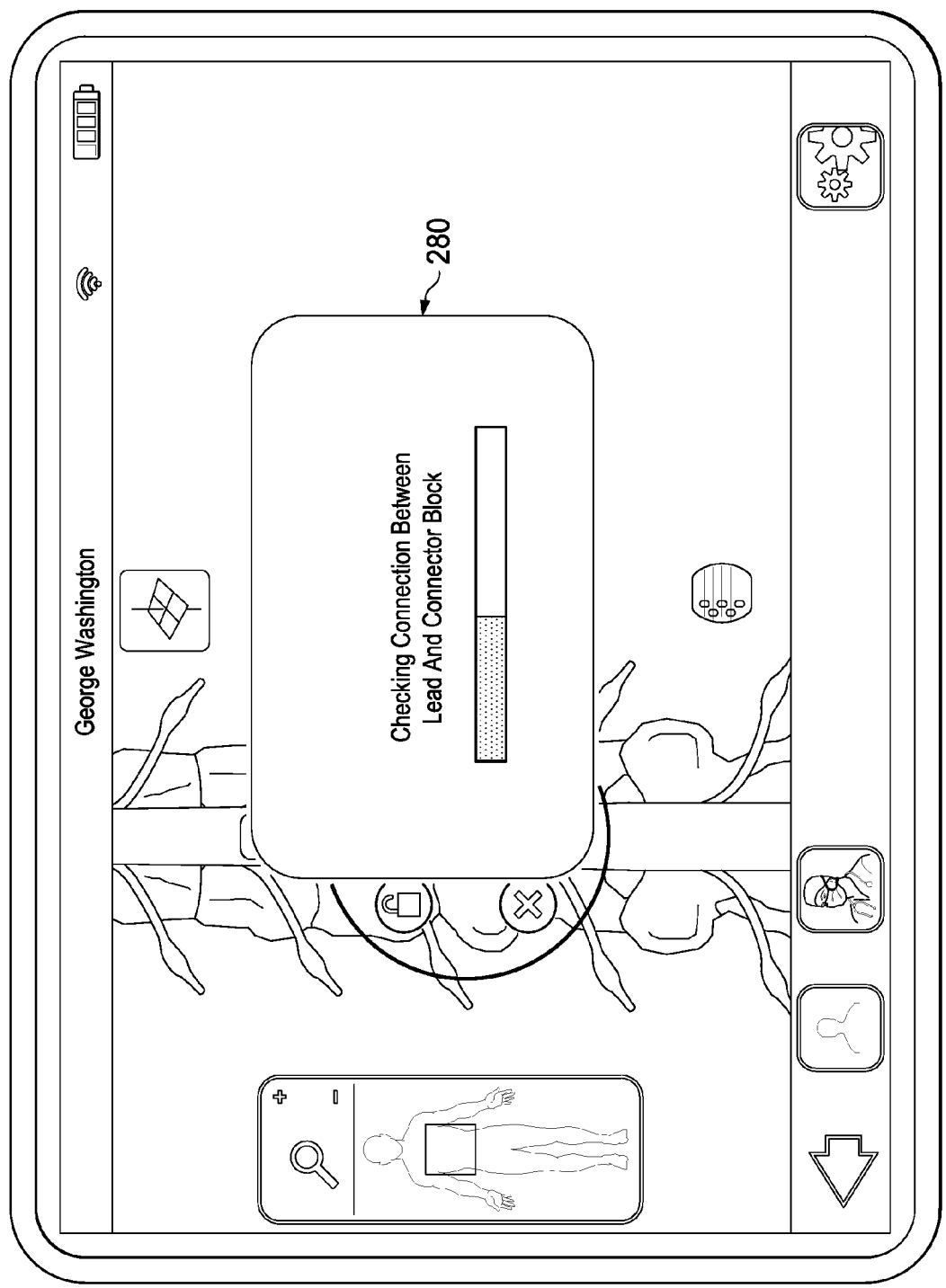

Referring now to FIG. 11, if the user chooses to establish the communications link, the clinician programmer will automatically check the connection health between the lead 140 and the IPG 170 (or the lead connector block 210 in embodiments where the lead connector block 210 is connected to the lead 140). While the connection health is being checked, a progress bar 280 may be displayed.

In some embodiments, the connection health is being verified by an impedance test. In more detail, for a high quality connection to exist between the lead 140 and the IPG 170 (or the lead connector block 210), each of the twelve connectors on the lead wire should make good contact with the electrodes of the IPG 170 (or the lead connector block 210). Unfortunately, since the IPG 170 and the lead connector block 210 are implanted inside a human body, fluids or other bodily materials may be pushed into the connection assembly or otherwise degrade the quality of the connections. These conditions are typically associated with an abnormal change in impedance values at the connection locations (i.e., the interface between the connectors on the lead wire and the electrodes of the IPG). According to the various aspects of the present disclosure, the IPG 170 (or the lead connector block 210) can perform impedance tests for each of the twelve connection locations.

Figure 12:
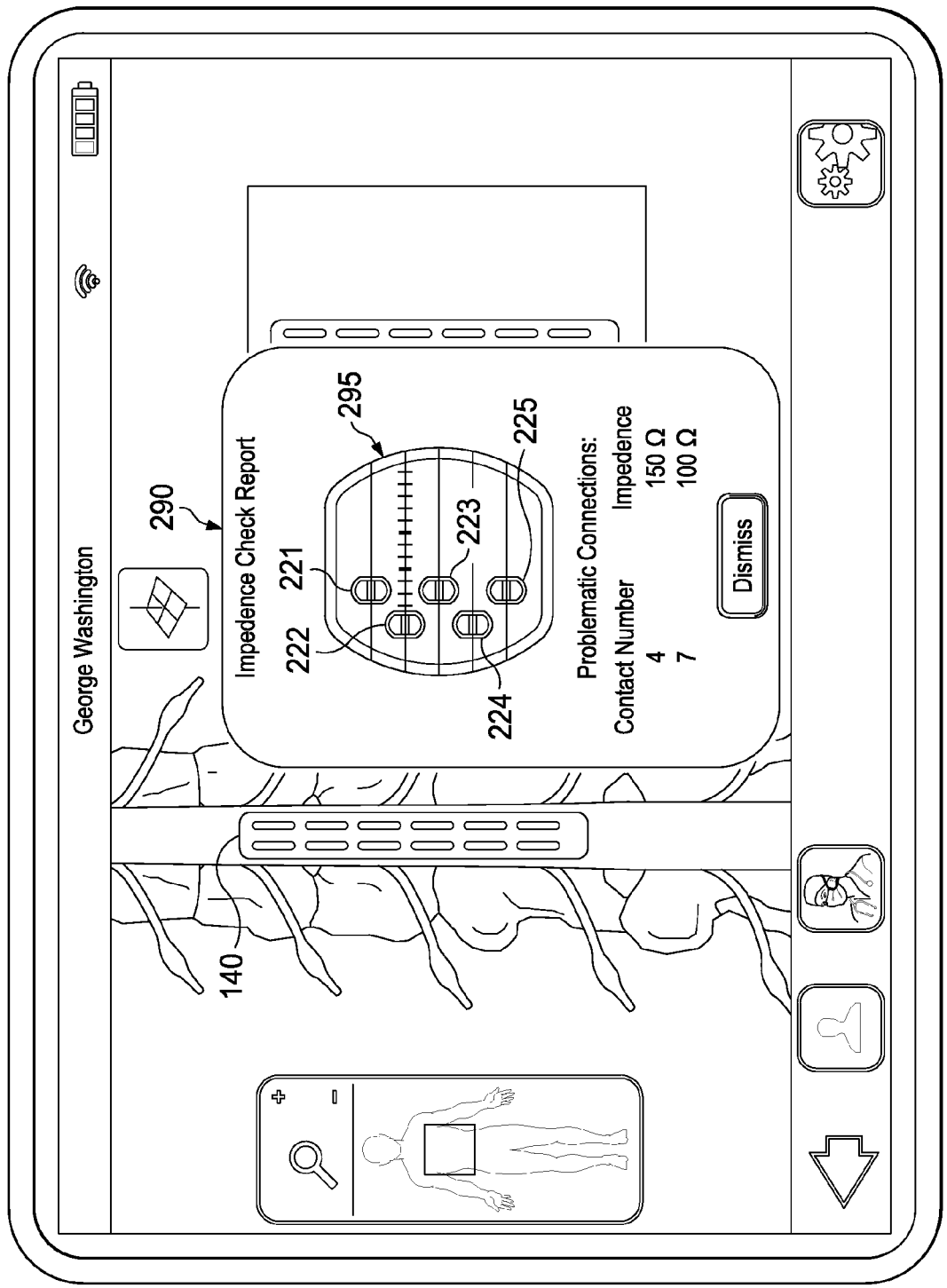

The results of the impedance test may then be relayed back to the clinician programmer, as shown in FIG. 12. In the embodiment shown in FIG. 12, the results from the impedance test are displayed in the form of an impedance check report 290. The impedance check report 290 displays the port/bore to which the connection is made with the lead (port 222 in this case). The connection status for each of the twelve contacts is also displayed via a visual mechanism 295, which includes twelve dots of one or more colors. Each of the twelve dots of the visual mechanism 295 corresponds to a respective one of the contacts (or the interface between the conductive connector on the lead wire and the electrode of the IPG).

The impedance check report further displays the specific problematic connections, which are the connections associated with contact numbers 4 and 7 in this case. The specific impedance values detected at these contact numbers may also be displayed (e.g. 150 ohms and 100 ohms in this case, respectively). Furthermore, to help the user visualize the status of the connections, the problematic contacts (i.e., numbers 4 and 7 in this case) may be displayed with a different color than the rest of the contacts in the visual mechanism 295. For example, while the healthy contacts are displayed in a green color, the problematic contacts 4 and 7 may be displayed in a red color.

It is understood that the clinician programmer of the present disclosure is capable of providing graphical simulations for devices that are not currently supported by the programmer. For example, after the clinician programmer has been released and deployed, a new pulse generator, lead, or lead connector block may become available. The clinician programmer does not currently have the information needed to provide graphical representations of these devices since they are new. However, the clinician programmer may download such information via a network (e.g., a cloud network or a remote database), an SD card or another portable memory storage device, or even by direct communication (which may be wireless) with the pulse generator. Regardless of how the clinician programmer retrieves the information associated with providing graphical representations of the pulse generator/lead/lead connector block, the clinician programmer can now provide graphical representations of these devices and the connections therewith in the same manner as discussed above.

Based on the discussions above, it can be seen that the clinician programmer of the present disclosure offers various advantages over existing clinician programmers and provides solutions to various problems associated with the lack of visualization of medical devices in the neurostimulation context.

One existing problem is that the connections between the lead(s) and the connector blocks or IPGs are not visually displayed, thereby forcing the user (e.g., healthcare professional) to memorize these connections. For example, users must mentally associate the implanted leads and the connection ports the leads are connected to. In comparison, the clinician programmer graphically represents the lead(s), IPG, the lead connector block, and the connections therebetween in a graphical user interface. As such, the user may readily refer to the user interface for the specific connections instead of relying only on memory. The graphical representations and recording of connections automatically tracks leads and their respective connection ports, thereby reducing user errors.

Another existing problem is that the information about connection quality is not displayed visually. In comparison, the clinician programmer herein displays connection quality information in a visual representation as well as in a written form (e.g., by text). Thus, the user can quickly identify which contacts are bad or becoming bad and take corresponding remedial action thereafter.

Yet another existing problem is that there was no way for the user to know whether a lead is being connected incorrectly or not. In comparison, the clinician programmer herein will prevent incorrect connections by only providing applicable options for connections. For example, in the case of the lead connector block having a plurality of ports, only the port(s) compatible with the lead will be allowed to establish a simulated connection therebetween. Thus, the user cannot mistakenly connect the lead to a wrong port that is incompatible with the lead in the simulation process provided by the graphical user interface discussed above.

Figure 13:
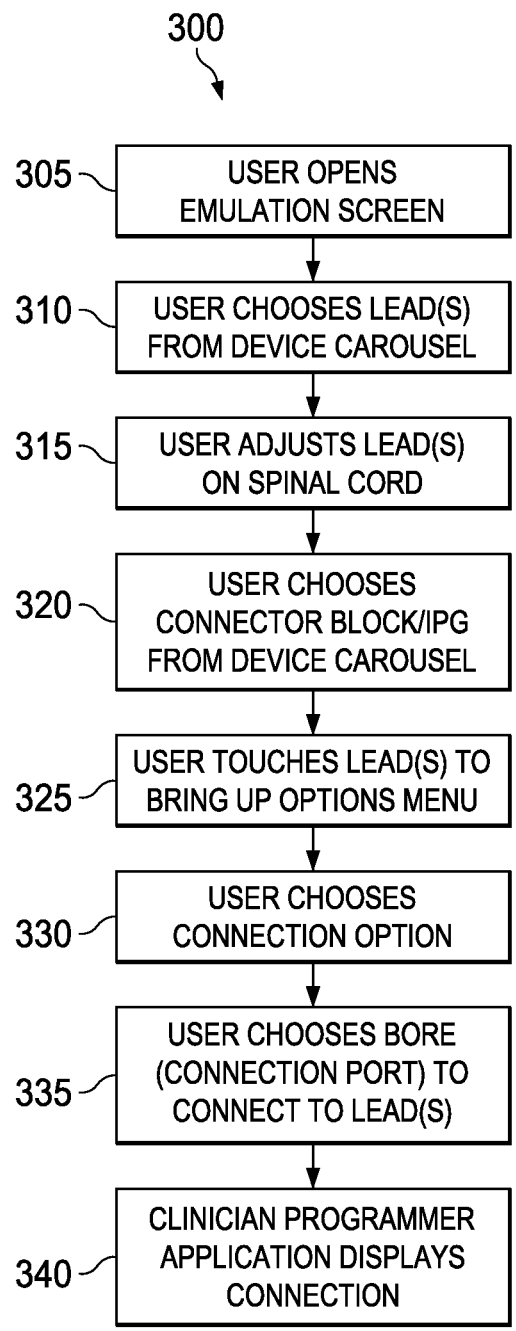
FIGS. 13-15 are flowcharts of methods for performing the various methods and processes according to the various aspects of the present disclosure.
Figure 14:
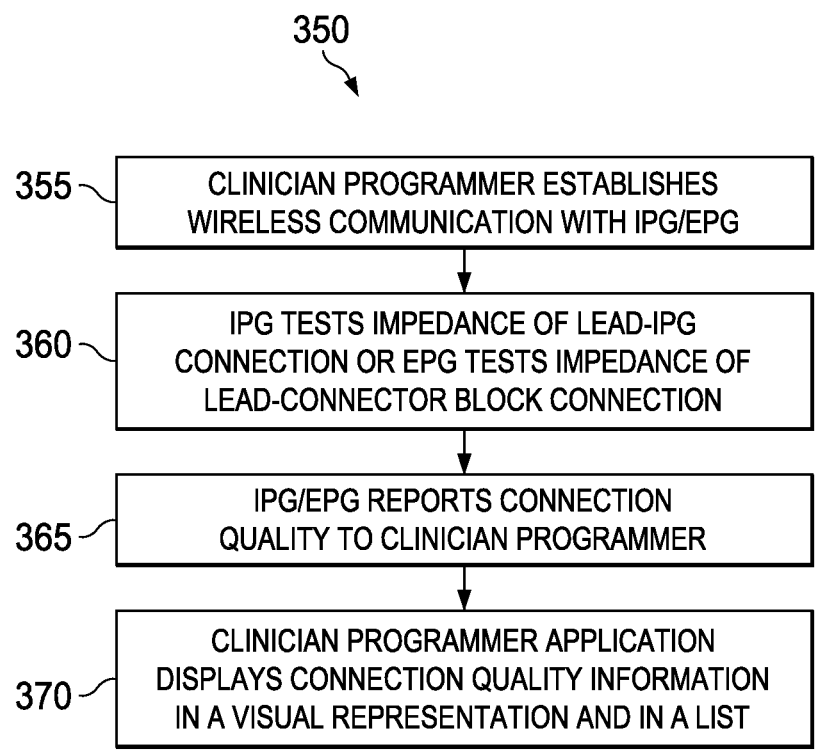
Figure 15:
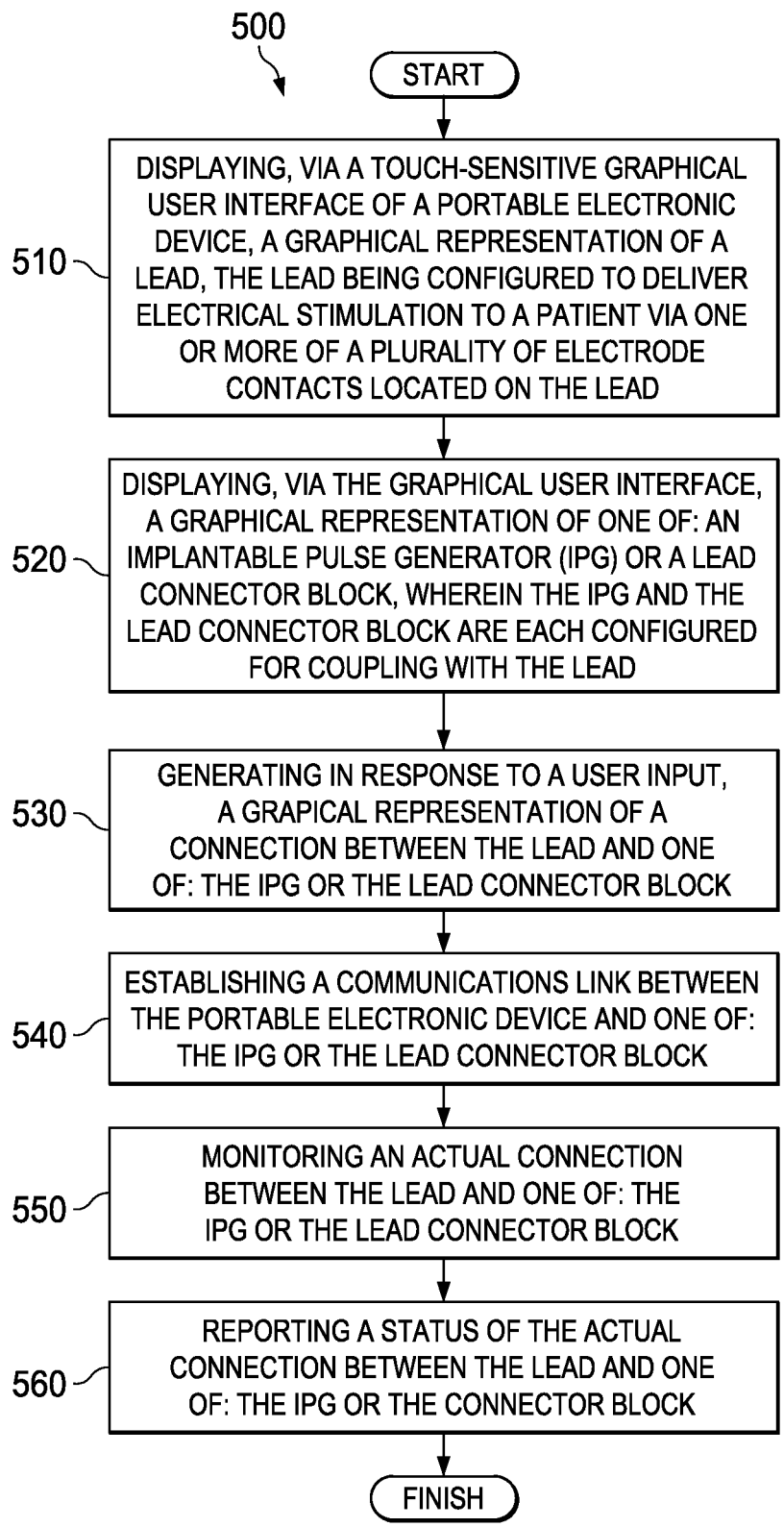

FIGS. 13-15 are simplified flowcharts illustrating the process and methods performed to carry out the various aspects of the present disclosure. It is understood that for each of these flowcharts, some of the process steps may only be briefly discussed, the illustrated steps need not necessarily be performed in sequential order as illustrated unless specifically specified, and that additional process steps (not illustrated) may be performed before, during, or after the illustrated process steps.

FIG. 13 is a flowchart illustrating a process 300 of using virtual representations and visual user feedback of connections according to various aspects of the present disclosure. The process 300 includes a step 305, in which the user opens an emulation screen on the clinician programmer. The process 300 continues with a step 310, in which the user chooses lead(s) from a virtual device carousel. The process 300 continues with a step 315, in which the user adjusts the lead(s) on a virtual representation of a spinal cord. The process 300 continues with a step 320, in which the user chooses a connector block or an IPG from the virtual device carousel. The process 300 continues with a step 325, in which the user touches the virtual representation of the lead(s) to bring up the display of an option menu. The process 300 continues with a step 330, in which the user chooses the connection option. The process 300 continues with a step 335, in which the user chooses the bore (connection port) on the IPG or the connector block to connect to the lead(s). The process 300 continues with a step 340, in which the clinician programmer application displays the simulated connections between the lead(s) and the IPG or the connector block.

FIG. 14 is a simplified flowchart illustrating a method 350 of showing connections quality between a lead and a pulse generator or a lead connector block according to various aspects of the present disclosure. The method 350 includes a step 355, in which the clinician programmer establishes wireless communication with an IPG/EPG. The method 350 continues with a step 360, in which the IPG tests the impedance of the lead-IPG connection, or the EPG tests the impedance of the lead-connector block connection. The method 350 continues with a step 365, in which the IPG/EPG reports the connection quality to the clinician programmer. The method 350 continues with a step 370, in which the clinician programmer application displays the connection quality information in a visual representation and in a list.

FIG. 15 is a simplified flowchart illustrating a method 500 of providing graphical representations of medical devices and connections between the medical devices. The method includes a step 510 of displaying, via a touch-sensitive graphical user interface of a portable electronic device, a graphical representation of a lead. The lead is configured to deliver electrical stimulation to a patient via one or more of a plurality of electrode contacts located on the lead. In some embodiments, the portable electronic device includes a clinician programmer or a tablet computer. The method includes a step 520 of displaying, via the graphical user interface, a graphical representation of one of: an implantable pulse generator (IPG) or a lead connector block. The IPG and the lead connector block are each configured for coupling with the lead. The method includes a step 530 of generating, in response to a user input, a graphical representation of a connection between the lead and one of: the IPG or the lead connector block. The method includes a step 540 of establishing a communications link between the portable electronic device and one of: the IPG or the lead connector block. The method includes a step 550 of monitoring an actual connection between the lead and one of: the IPG or the lead connector block. The method includes a step 560 of reporting a status of the actual connection between the lead and one of: the IPG or the connector block.

In some embodiments, the step 520 of displaying the graphical representation of the lead comprises displaying the graphical representation of the lead over a graphical representation of a human spinal cord.

In some embodiments, the step 530 comprises: indicating, for the IPG or the lead connector block, a plurality of ports available for connection with the lead; prompting the user to select one of the available ports for connection with the lead; and establishing the graphical representation of the connection between the selected port and the lead.

In some embodiments, the step 530 comprises displaying an animation sequence that shows a graphical representation of a lead wire of the lead being inserted into a port of one of: the IPG or the lead connector block. In some embodiments, the step of displaying the animation sequence comprises preventing the graphical representation of the lead wire from being inserted into the port until after the actual connection is made between the lead and the one of: the IPG or the lead connector block. In some embodiments, the method 500 further comprises a step of providing a feedback to the user when the graphical representation of the lead wire has been successfully inserted into the port. The feedback is one of: an audible feedback, a visual feedback, and a tactile feedback.

In some embodiments, the step 550 comprises performing an impedance check for each of the electrode contacts on the lead.

In some embodiments, the step 560 comprises visually indicating electrode contacts that are problematic.

Figure 16:
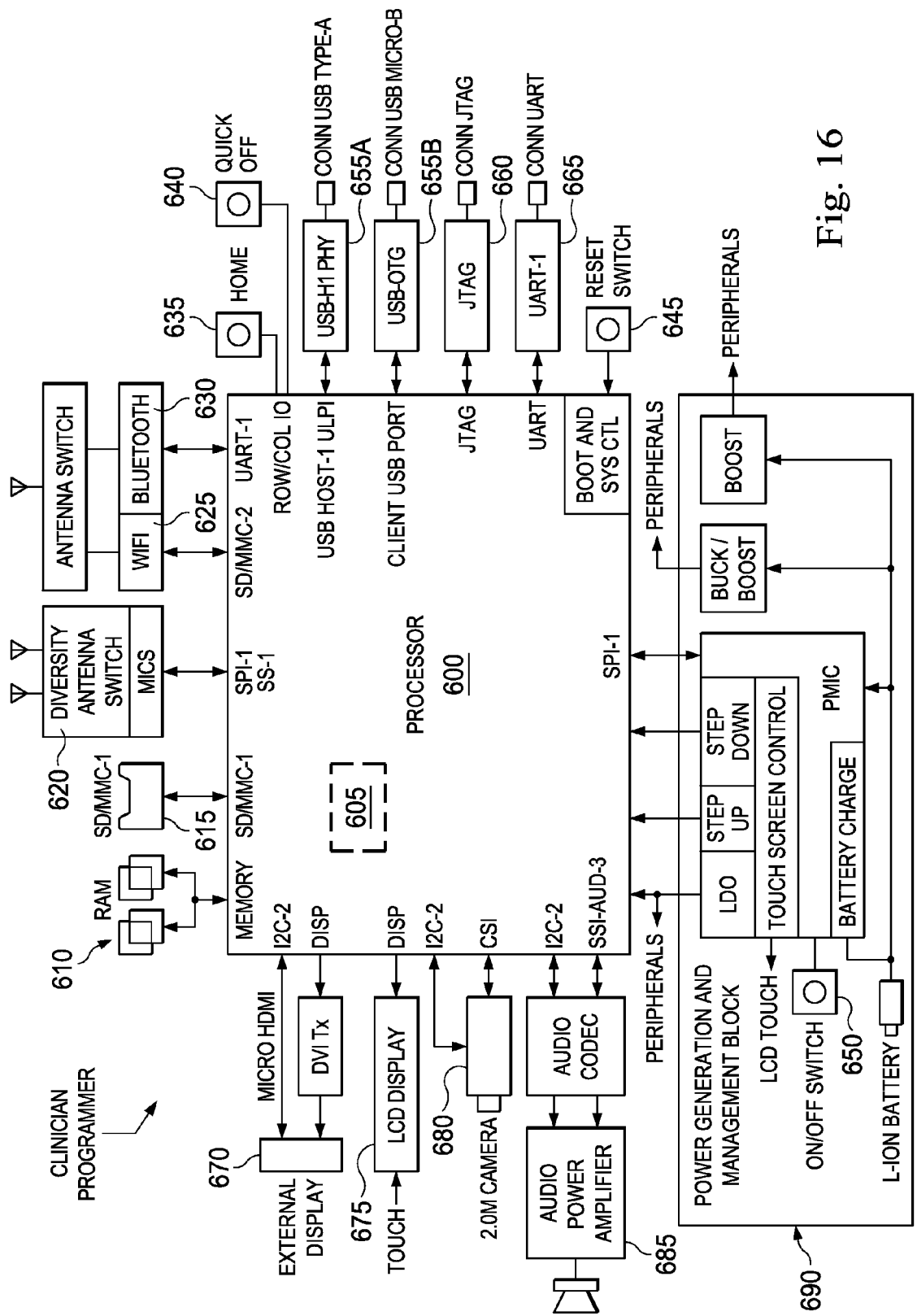
FIG. 16 is a simplified block diagram of an electronic programmer according to various aspects of the present disclosure.

FIG. 16 shows a block diagram of one embodiment of the electronic programmer discussed herein. For example, the electronic programmer may be a clinician programmer (CP) configured to provide the graphical representations of medical devices and connections between the medical devices as discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 16, the CP includes a processor 600. The processor 600 controls the CP. In one construction, the processor 600 is an applications processor model i.MX515 available from Free scale Semiconductor®. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet dated August 2010 and published by Free scale Semiconductor® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 16 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 16.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 16.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 16) may also be included for data transfer.

It is understood that a patient programmer may be implemented in a similar manner as the clinician programmer shown in FIG. 16.

Figure 17:
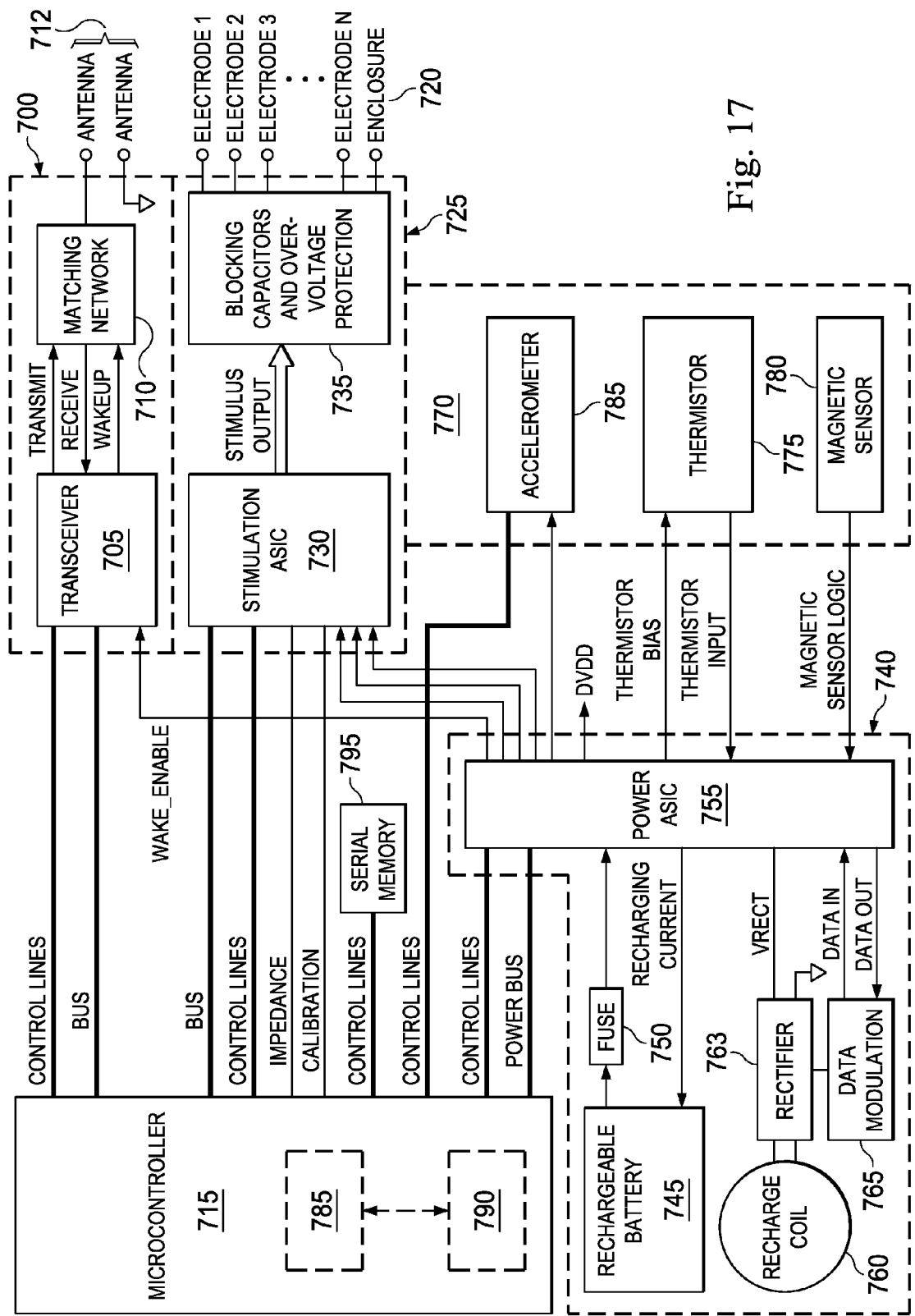
FIG. 17 is a simplified block diagram of an implantable medical device according to various aspects of the present disclosure.

FIG. 17 shows a block diagram of one embodiment of an implantable medical device. In the embodiment shown in FIG. 17, the implantable medical device includes an implantable pulse generator (IPG). The IPG includes a printed circuit board ("PCB") that is populated with a plurality of electrical and electronic components that provide power, operational control, and protection to the IPG. With reference to FIG. 17, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 17, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 17 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Referring now to FIG. 18, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 17), an implantable lead, a charger, or portions thereof. It is understood that each of the medical devices 810 may be a different type of medical device. In other words, the medical devices 810 need not be the same type of medical device.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 16. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 18 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, electronic data, such as pain and stimulation maps (collectively referred to as sensation maps) may be uploaded from the electronic programmer 820A to the database 900. The sensation maps are discussed in more detail in provisional U.S. Patent Application No. 61/695,407, filed on Aug. 31, 2012, entitled "Method and System of Producing 2D Representations of 3D Pain and Stimulation Maps and Implant Models on a Clinician Programmer," and provisional U.S. Patent Application No. 61/695,721, filed on Aug. 31, 2012, entitled "Method and System of Creating, Displaying, and Comparing Pain and Stimulation Maps," and provisional U.S. Patent Application No. 61/695,676, filed on Aug. 31, 2012, entitled "Method and System of Adjusting 3D Models of Patients on a Clinician Programmer," the disclosure of each of which is hereby incorporated by reference in its entirety.

The sensation maps saved in the database 900 may thereafter be downloaded by any of the other electronic programmers 820B-820N communicatively coupled to it, assuming the user of these programmers has the right login permissions. For example, after the 2D sensation map is generated by the electronic programmer 820A and uploaded to the database 900. That 2D sensation map can then be downloaded by the electronic programmer 820B, which can use the downloaded 2D sensation map to reconstruct or recreate a 3D sensation map. In this manner, a less data-intensive 2D sensation map may be derived from a data-heavy 3D sensation map, sent to a different programmer through the database, and then be used to reconstruct the 3D sensation map. The sensation maps are used herein merely as an example to illustrate the transfer of electronic data in the medical infrastructure 800. Other types of electronic data may also be transferred in a similar (or different) manner.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 19B:
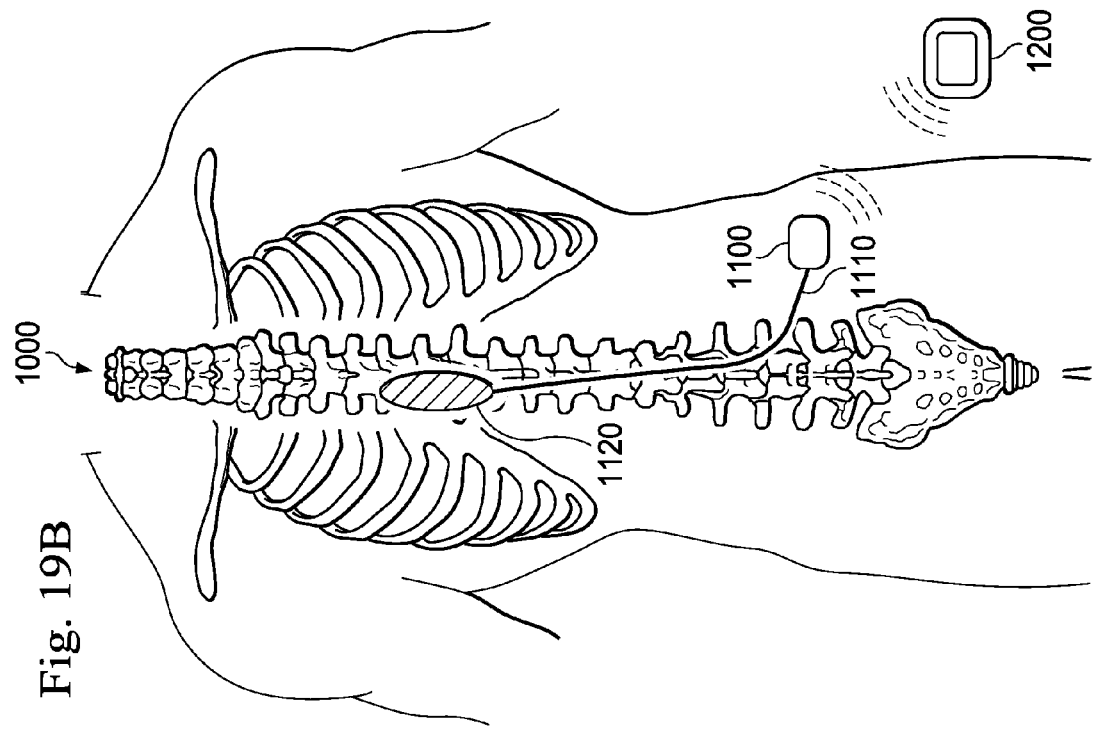
FIGS. 19A and 19B are side and posterior views of a human spine, respectively.
Figure 19A:
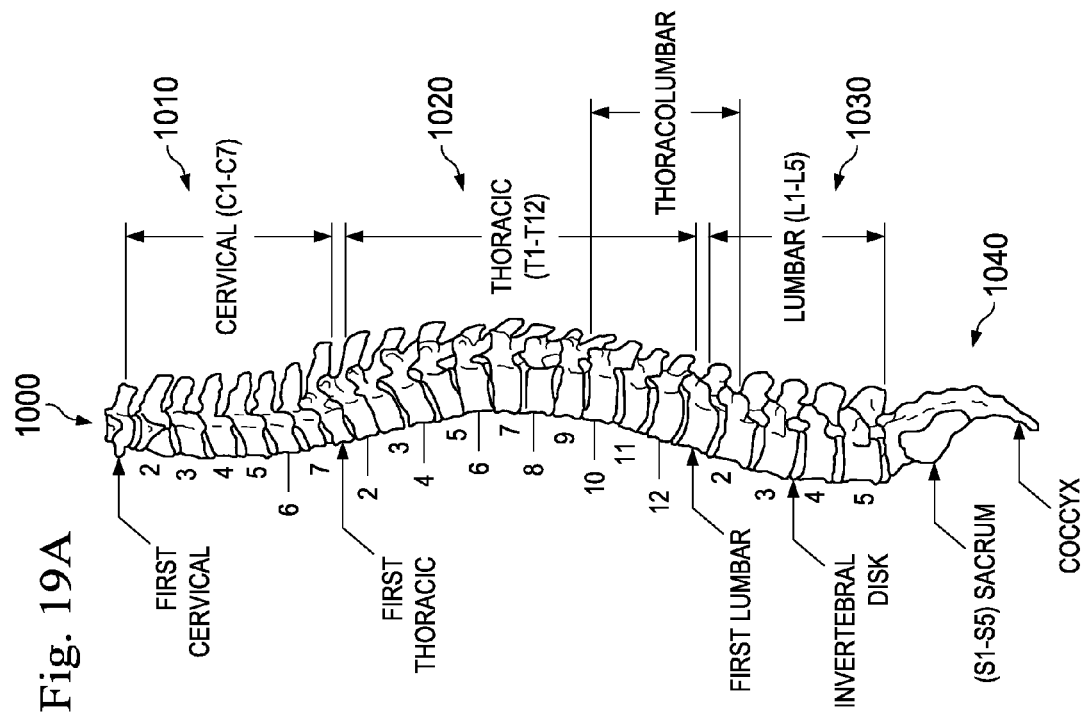

FIG. 19A is a side view of a spine 1000, and FIG. 19B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 19B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 16.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An electronic device configured to provide graphical representations of medical devices and connections between the medical devices, the electronic device comprising:
   a touch-sensitive display configured to receive input from a user and display an output to the user;
   a memory storage component configured to store programming code; and
   a computer processor configured to execute the programming code to perform the following tasks:
   displaying, via the touch-sensitive display, a graphical representation of a lead, the lead being configured to deliver electrical stimulation to a patient via one or more of a plurality of electrode contacts located on the lead;
   displaying, via the touch-sensitive display, a graphical representation of one of: an implantable pulse generator (IPG) or a lead connector block, wherein the IPG and the lead connector block are each configured for coupling with the lead;
   generating, in response to a user input, a graphical representation of a connection between the lead and one of: the IPG or the lead connector block;
   monitoring an actual connection between the lead and one of: the IPG or the lead connector block; and
   reporting a status of the actual connection between the lead and one of: the IPG or the connector block.

2. The electronic device of claim 1, wherein the tasks further comprise: before the monitoring, establishing a communications link between the electronic device and one of: the IPG or the lead connector block.

3. The electronic device of claim 1, wherein the monitoring of the connection comprises performing an impedance check for each of the electrode contacts on the lead.

4. The electronic device of claim 1, the reporting of the status comprises visually indicating electrode contacts that are problematic.

5. The electronic device of claim 1, wherein the generating comprises:
   indicating, for the IPG or the lead connector block, a plurality of ports available for connection with the lead;
   prompting the user to select one of the available ports for connection with the lead; and
   establishing the graphical representation of the connection between the selected port and the lead.

6. The electronic device of claim 1, wherein the generating comprises displaying an animation sequence that shows a graphical representation of a lead wire of the lead being inserted into a port of one of: the IPG or the lead connector block.

7. The electronic device of claim 6, wherein the tasks further comprise: providing a feedback to the user when the graphical representation of the lead wire has been successfully inserted into the port, wherein the feedback is one of: an audible feedback, a visual feedback, and a tactile feedback.

8. The electronic device of claim 6, wherein the displaying the animation sequence comprises preventing the graphical representation of the lead wire from being inserted into the port until after the actual connection is made between the lead and the one of: the IPG or the lead connector block.

9. The electronic device of claim 1, wherein the displaying of the graphical representation of the lead comprises displaying the graphical representation of the lead over a graphical representation of a human spinal cord.

10. The electronic device of claim 1, wherein the electronic device comprises a clinician programmer or a tablet computer.

11. A medical system, comprising:
    a pulse generator configured to generate pulses as part of an electrical stimulation therapy for a patient;
    a lead having a plurality of electrode contacts, the lead being configured for coupling with the pulse generator and for delivering the pulses to the patient via one or more of the electrode contacts; and
    a clinician programmer configured to provide a graphical representation of the pulse generator, the lead, and connections therebetween, wherein the clinician programmer includes one or more processors and a non-transitory, tangible machine-readable storage medium storing a computer application, wherein the computer application contains machine-readable instructions that when executed electronically by the one or more processors, perform the following actions:
       displaying, via a touch-sensitive graphical user interface of the clinician programmer, a graphical representation of the pulse generator, a graphical representation of the lead;
       generating, in response to a user input, a graphical representation of a connection between the lead and the pulse generator;
       monitoring an actual connection between the lead and the pulse generator; and
       reporting a status of the actual connection between the lead and the pulse generator.

12. The medical system of claim 11, wherein the actions further comprise: before the monitoring, establishing a communications link between the portable electronic device and the pulse generator.

13. The medical system of claim 11, wherein the monitoring of the connection comprises performing an impedance check for each of the electrode contacts on the lead.

14. The medical system of claim 11, the reporting of the status comprises visually indicating electrode contacts that are problematic.

15. The medical system of claim 11, wherein the generating comprises:
   indicating, for the pulse generator, a plurality of ports available for connection with the lead;
   prompting the user to select one of the available ports for connection with the lead; and
   establishing the graphical representation of the connection between the selected port and the lead.

16. The medical system of claim 11, wherein the generating comprises displaying an animation sequence that shows a graphical representation of a lead wire of the lead being inserted into a port of the pulse generator.

17. The medical system of claim 16, wherein the actions further comprise: providing a feedback to the user when the graphical representation of the lead wire has been successfully inserted into the port, wherein the feedback is one of: an audible feedback, a visual feedback, and a tactile feedback.

18. The medical system of claim 16, wherein the displaying the animation sequence comprises preventing the graphical representation of the lead wire from being inserted into the port until after the actual connection is made between the lead and the pulse generator.

19. The medical system of claim 11, wherein the displaying the graphical representation of the lead comprises displaying the graphical representation of the lead over a graphical representation of a human spinal cord.

20. The medical system of claim 11, wherein the pulse generator includes one of: an implantable pulse generator (IPG) or an external pulse generator (EPG).

21. The medical system of claim 11, wherein:
    the pulse generator is the EPG;
    the EPG includes a lead connector block;
    the displaying comprises displaying a graphical representation of the lead connector block as the representation of the EPG; and
    the generating comprises generating a graphical representation of a connection between the lead and the lead connector block.

22. A method of providing graphical representations of medical devices and connections between the medical devices, the method comprising:
    displaying, via a touch-sensitive graphical user interface of a portable electronic device, a graphical representation of a lead, the lead being configured to deliver electrical stimulation to a patient via one or more of a plurality of electrode contacts located on the lead;
    displaying, via the graphical user interface, a graphical representation of one of: an implantable pulse generator (IPG) or a lead connector block, wherein the IPG and the lead connector block are each configured for coupling with the lead;
    generating, in response to a user input, a graphical representation of a connection between the lead and one of: the IPG or the lead connector block;
    monitoring an actual connection between the lead and one of: the IPG or the lead connector block; and
    reporting a status of the actual connection between the lead and one of: the IPG or the connector block.

23. The method of claim 22, further comprising: before the monitoring, establishing a communications link between the portable electronic device and one of: the IPG or the lead connector block.

24. The method of claim 22, wherein the monitoring of the connection comprises performing an impedance check for each of the electrode contacts on the lead.

25. The method of claim 22, the reporting of the status comprises visually indicating electrode contacts that are problematic.

26. The method of claim 22, wherein the generating comprises:
    indicating, for the IPG or the lead connector block, a plurality of ports available for connection with the lead;
    prompting the user to select one of the available ports for connection with the lead; and
    establishing the graphical representation of the connection between the selected port and the lead.

27. The method of claim 22, wherein the generating comprises displaying an animation sequence that shows a graphical representation of a lead wire of the lead being inserted into a port of one of: the IPG or the lead connector block.

28. The method of claim 27, further comprising: providing a feedback to the user when the graphical representation of the lead wire has been successfully inserted into the port, wherein the feedback is one of: an audible feedback, a visual feedback, and a tactile feedback.

29. The method of claim 27, wherein the displaying the animation sequence comprises preventing the graphical representation of the lead wire from being inserted into the port until after the actual connection is made between the lead and the one of: the IPG or the lead connector block.

30. The method of claim 22, wherein the displaying the graphical representation of the lead comprises displaying the graphical representation of the lead over a graphical representation of a human spinal cord.

31. The method of claim 22, wherein the portable electronic device comprises a clinician programmer or a tablet computer.

32. An electronic apparatus for providing graphical representations of medical devices and connections between the medical devices, the electronic apparatus comprising:
    user interface means for communicating with a user;
    memory storage means for storing executable instructions; and
    computer processor means for executing the instructions to perform:
        displaying, via the user interface means, a graphical representation of a lead over a graphical representation of a human spinal cord, the lead being configured to deliver electrical stimulation to a patient via one or more of a plurality of electrode contacts located on the lead;
        displaying, via the user interface means, a graphical representation of one of: an implantable pulse generator (IPG) or a lead connector block, wherein the IPG and the lead connector block are each configured for coupling with the lead;
        generating, in response to a user input, a graphical representation of a connection between the lead and one of: the IPG or the lead connector block;
        establishing a communications link with one of: the IPG or the lead connector block;
        monitoring an actual connection between the lead and one of: the IPG or the lead connector block, wherein the monitoring comprises performing an impedance check for each of the electrode contacts on the lead; and
        reporting a status of the actual connection between the lead and one of: the IPG or the connector block, wherein the reporting comprises visually indicating electrode contacts that are problematic.

33. The electronic apparatus of claim 32, wherein the generating comprises:
    indicating, for the IPG or the lead connector block, a plurality of ports available for connection with the lead;
    prompting the user to select one of the available ports for connection with the lead; and
    establishing the graphical representation of the connection between the selected port and the lead.

34. The electronic apparatus of claim 32, wherein the generating comprises displaying an animation sequence that shows a graphical representation of a lead wire of the lead being inserted into a port of one of: the IPG or the lead connector block.

35. The electronic apparatus of claim 34, further comprising: providing a feedback to the user when the graphical representation of the lead wire has been successfully inserted into the port, wherein the feedback is one of: an audible feedback, a visual feedback, and a tactile feedback.

36. The electronic apparatus of claim 34, wherein the displaying the animation sequence comprises preventing the graphical representation of the lead wire from being inserted into the port until after the actual connection is made between the lead and the one of: the IPG or the lead connector block.

* * * * *